(12) United States Patent
Harris, Jr.

(10) Patent No.: US 12,182,956 B2
(45) Date of Patent: Dec. 31, 2024

(54) SYSTEMS AND METHODS OF USING THREE-DIMENSIONAL IMAGE RECONSTRUCTION TO AID IN ASSESSING BONE OR SOFT TISSUE ABERRATIONS FOR ORTHOPEDIC SURGERY

(71) Applicant: MicroPort Orthopedics Holdings Inc., Arlington, TN (US)

(72) Inventor: Brian R. Harris, Jr., Cordova, TN (US)

(73) Assignee: MicroPort Orthopedics Holdings Inc., Arlington, TN (US)

( * ) Notice: Subject to any disclaimer, the term of this patent is extended or adjusted under 35 U.S.C. 154(b) by 0 days.

(21) Appl. No.: 17/835,894

(22) Filed: Jun. 8, 2022

(65) Prior Publication Data

US 2023/0005232 A1    Jan. 5, 2023

Related U.S. Application Data

(60) Provisional application No. 63/217,567, filed on Jul. 1, 2021.

(51) Int. Cl.
*G06T 19/20* (2011.01)
*A61B 6/46* (2024.01)
(Continued)

(52) U.S. Cl.
CPC ............. *G06T 19/20* (2013.01); *A61B 6/466* (2013.01); *A61B 6/505* (2013.01); *A61B 6/582* (2013.01);
(Continued)

(58) Field of Classification Search
CPC .................. G06T 19/20; G06T 7/0014; G06T 2207/10116; G06T 2207/20084;
(Continued)

(56) References Cited

U.S. PATENT DOCUMENTS 6,891,518 B2   5/2005   Sauer et al.
6,919,867 B2   7/2005   Sauer
(Continued)

FOREIGN PATENT DOCUMENTS

CN    102599960    8/2015
CN    105266897    1/2016
(Continued)

OTHER PUBLICATIONS

Vincent Masse, Raju S. & Ghate, "Using Standard X-ray Images to Create 3D Digital Bone Models and Patient-Matched Guides for Aiding Implant Positioning and Sizing in Total Knee Arthroplasty," Computer Assisted Surgery, Mar. 15, 2021, 36:1, 31-40.
(Continued)

*Primary Examiner* — Vijay Shankar
(74) *Attorney, Agent, or Firm* — Robert J. Hornung

(57) ABSTRACT

Systems and methods for calculating external bone loss for alignment of pre-diseased joints comprising: generating a three-dimensional ("3D") computer model of an operative area from at least two two-dimensional ("2D") radiographic images, wherein at least a first radiographic image is captured at a first position, and wherein at least a second radiographic image is captured at a second position, and wherein the first position is different than the second position; identifying an area of bone loss on the 3D computer model; and applying a surface adjustment algorithm to calculate an external missing bone surface fitting the area of bone loss.

18 Claims, 18 Drawing Sheets

(51) Int. Cl.
| | |
|---|---|
| *A61B 6/50* | (2024.01) |
| *A61B 6/58* | (2024.01) |
| *A61B 34/10* | (2016.01) |
| *B29C 64/386* | (2017.01) |
| *B33Y 50/00* | (2015.01) |
| *G06F 3/01* | (2006.01) |
| *G06T 7/00* | (2017.01) |
| *G16H 30/40* | (2018.01) |
| *G16H 50/20* | (2018.01) |
| *G16H 50/50* | (2018.01) |
| *A61B 90/00* | (2016.01) |
| *B29K 77/00* | (2006.01) |
| *B29L 31/40* | (2006.01) |
| *B33Y 80/00* | (2015.01) |

(52) U.S. Cl.
CPC ............ *A61B 34/10* (2016.02); *B29C 64/386* (2017.08); *B33Y 50/00* (2014.12); *G06F 3/011* (2013.01); *G06T 7/0014* (2013.01); *G16H 30/40* (2018.01); *G16H 50/20* (2018.01); *G16H 50/50* (2018.01); *A61B 2034/105* (2016.02); *A61B 2090/365* (2016.02); *A61B 2090/367* (2016.02); *B29K 2077/00* (2013.01); *B29L 2031/40* (2013.01); *B33Y 80/00* (2014.12); *G06T 2207/10116* (2013.01); *G06T 2207/20084* (2013.01); *G06T 2207/30008* (2013.01); *G06T 2210/44* (2013.01); *G06T 2219/2021* (2013.01)

(58) Field of Classification Search
CPC ....... G06T 2207/30008; G06T 2210/44; G06T 2219/2021; G06T 7/337; G06T 7/50; G06T 11/003; G06F 3/011; G06F 3/015; A61B 6/466; A61B 6/505; A61B 6/582; A61B 34/10; A61B 2034/105; A61B 2090/365; A61B 2090/367; A61B 17/155; A61B 2034/107; A61B 2034/2048; A61B 2090/376; A61B 2034/101; A61B 2034/108; A61B 90/36; A61B 90/37; A61B 2017/00707; B29C 64/386; B33Y 50/00; B33Y 80/00; G16H 30/40; G16H 50/20; G16H 50/50; G16H 30/20; B29K 2077/00; B29L 2031/40; G06N 3/0464; G06N 3/045; G06N 3/0475; G06N 3/048; G06N 3/094; G06N 3/096; G06N 3/04; A61F 2/3609; A61F 2/468; A61F 2002/4633; G06V 10/82; G06V 2201/033
See application file for complete search history.

(56) References Cited

U.S. PATENT DOCUMENTS

| | | | |
|---|---|---|---|
| 7,511,736 B2 | 3/2009 | Benton | |
| 7,618,451 B2 | 11/2009 | Berez et al. | |
| 7,771,436 B2 | 8/2010 | Moctezuma De La Barrera et al. | |
| 7,774,044 B2 | 8/2010 | Sauer et al. | |
| 7,806,896 B1 | 10/2010 | Bonutti | |
| 8,485,038 B2 | 7/2013 | Sengupta et al. | |
| 8,543,338 B2 | 9/2013 | Bronstein et al. | |
| 8,634,897 B2 | 1/2014 | Simon et al. | |
| 8,657,809 B2 | 2/2014 | Schoepp | |
| 8,842,893 B2 | 9/2014 | Teichman et al. | |
| 8,963,957 B2 | 2/2015 | Skarulis | |
| 9,089,342 B2 | 7/2015 | Carroll et al. | |
| 9,439,622 B2 | 9/2016 | Case et al. | |
| 9,547,940 B1 | 1/2017 | Sun et al. | |
| 9,610,056 B2 | 4/2017 | Lavallee et al. | |
| 9,681,925 B2 | 6/2017 | Azar et al. | |
| 9,901,463 B2 | 2/2018 | Mahfouz | |
| 10,166,109 B2 | 1/2019 | Ferko | |
| 10,258,426 B2 | 4/2019 | Silva et al. | |
| 10,510,155 B1 | 12/2019 | Islam et al. | |
| 10,617,474 B2* | 4/2020 | Karlsson | A61F 2/32 |
| 10,722,310 B2 | 7/2020 | Luby | |
| 10,940,021 B2 | 3/2021 | Mahfouz | |
| 11,076,872 B2 | 8/2021 | Wilkinson | |
| 11,224,483 B2* | 1/2022 | Steinberg | A61B 90/36 |
| 11,423,603 B2 | 8/2022 | Sutton et al. | |
| 11,439,469 B2 | 9/2022 | Poltaretskyi et al. | |
| 11,621,086 B2* | 4/2023 | Spångberg | G16H 20/40 |
| | | | 382/131 |
| 11,648,405 B2* | 5/2023 | Crites-Bachert | A61N 1/372 |
| | | | 606/129 |
| 11,751,946 B2* | 9/2023 | Gangwar | G06T 7/73 |
| | | | 345/418 |
| 2008/0114370 A1 | 5/2008 | Schoenefeld | |
| 2008/0167550 A1 | 7/2008 | Weiser et al. | |
| 2009/0306679 A1 | 12/2009 | Murphy | |
| 2011/0071533 A1 | 3/2011 | Metzger et al. | |
| 2011/0236868 A1 | 9/2011 | Bronstein et al. | |
| 2012/0065640 A1 | 3/2012 | Metzger et al. | |
| 2013/0060146 A1 | 3/2013 | Yang et al. | |
| 2013/0117377 A1 | 5/2013 | Miller | |
| 2013/0310838 A1 | 11/2013 | Kurtz | |
| 2014/0013565 A1 | 1/2014 | MacDonald et al. | |
| 2014/0013566 A1 | 1/2014 | MacDonald | |
| 2016/0008143 A1 | 1/2016 | Mahfouz | |
| 2016/0026253 A1 | 1/2016 | Bradski et al. | |
| 2016/0228193 A1 | 8/2016 | Moctezuma de la Barrera et al. | |
| 2018/0168740 A1 | 6/2018 | Ryan et al. | |
| 2018/0177600 A1 | 6/2018 | Karlsson et al. | |
| 2018/0185100 A1 | 7/2018 | Weinstein et al. | |
| 2019/0008532 A1 | 1/2019 | Fitz et al. | |
| 2019/0262078 A1 | 8/2019 | Lang | |
| 2019/0380792 A1 | 12/2019 | Poltaretskyi et al. | |
| 2020/0138522 A1 | 5/2020 | Tikka | |
| 2020/0375666 A1 | 12/2020 | Murphy | |
| 2020/0405399 A1 | 12/2020 | Steinberg et al. | |
| 2022/0096245 A1 | 3/2022 | Sun et al. | |

FOREIGN PATENT DOCUMENTS

| | | |
|---|---|---|
| WO | 2012154534 | 11/2012 |
| WO | 2014120909 | 8/2014 |
| WO | 2016078919 | 5/2016 |
| WO | 2017066373 | 4/2017 |
| WO | 2018078017 | 4/2017 |
| WO | 2017200444 | 11/2017 |
| WO | 2021245093 | 12/2021 |

OTHER PUBLICATIONS

Tanguy Roudaut, Partial European Search Report and Written Opinion for EP app, No. 22182089, Feb. 23, 2023, Munich, Germany.

S.Hosseinian, H. Arefi, Photogrammetry in 3D Modelling of Human Bone Structures From Radiographs, International Archives of the Photogrammetry, Remote Sensing and Spatial Information Sciences, vol. XLII-2/W4, 2017 2nd International ISPRS Workshop on PSBB, May 15-17, 2017, Moscow, Russia.

Fausto Milletari, et. al., V-Net: Fully Convolutional Neural Networks for Volumetric Medical Image Segmentation., arXiv:1606.04797v1 [cs.CV] Jun. 15, 2016.

J. C. K. Chow, Modelling Errors in X-Ray Fluoroscopic Imaging Systems Using Photogrammetric Bundle Adjustment With a Data-Driven Self-Calibration Approach, The International Archives of the Photogrammetry, Remote Sensing and Spatial Information Sciences, vol. XLII-1, 2018 ISPRS TC I Mid-term Symposium "Innovative Sensing—From Sensors to Methods and Applications", Oct. 10-12, 2018, Karlsruhe, Germany.

Dr. F. G. Lippert III, M.D., An Analytical Approach to X-Ray Photogrammetry, Photogrammetric Engineering and Remote Sensing, vol. 43, No. 12, Dec. 1977, pp. 1503-1510. S. A. Veress, Ds.C., University of Washington, Seattle, WA 98195.

(56) References Cited

OTHER PUBLICATIONS

Avi-Ben-Cohen, Retinal layers segmentation using Fully Convolutional Network in OCT images.

Yoni Kasten, End-To-End Convolutional Neural Network for 3D Reconstruction of Knee Bones From Bi-Planar X-Ray Images, arXiv:2004.00871v2 [eess.IV] Aug. 12, 2020.

Ilya Kovler, Haptic computer-assisted patient-specific preoperative planning for orthopedic fractures surgery, Int J Cars DOI 10.1007/s11548-015-1162-9.

Sandor A. Veress, X-Ray Photogrammetry, State of The Art, University of Washington Seattle, WA 98195 United States IPRS Commission V.

Zimmer Biomet, Image Acquisition Protocol for X-PSI™ Knee System, 2018.

Thomas, Shane, International Search Report for PCT/US22/77111, Dec. 28, 2022, USPTO as ISA, Alexandria, Virginia, USA.

Thomas, Shane, Written Opinion of the International Searching Authority for PCT/US22/77111, Dec. 28, 2022, USPTO as ISA, Alexandria, Virginia, USA.

Matos, Taina, International Search Report for PCT/US22/77133, Dec. 8, 2022, USPTO as ISA, Alexandria, Virginia, USA.

Matos, Taina, Written Opinion of the International Searching Authority for PCT/US22/77133, Dec. 8, 2022, USPTO as ISA, Alexandria, Virginia, USA.

Thomas, Shane, International Search Report for PCT/US22/73868, Oct. 11, 2022, USPTO as ISA, Alexandria, Virginia, USA.

Thomas, Shane, Written Opinion of the International Searching Authority for PCT/US22/73868, Oct. 11, 2022, USPTO as ISA, Alexandria, Virginia, USA.

Roudaut, Tanguy, Invitation Pursuant to Rule 63(1)EPC, EPO Prosecution Document, Nov. 16, 2022, European Patent Office, Munich, Germany.

Roudaut, Tanguy, Communication pursuant to Article 94(3) EPC, European Search Report, Nov. 23, 2023, 11 pages, European Patent Office, Munich Germany.

Yilmaz, Ozgun, Supplementary European Search Report (art. 153(7) EPC) and European Search Opinion, Oct. 4, 2024, Munich, Germany.

A Uneri et. al., "Known-composent 3D-2D registration for quality assurance of spine surgery pedicle screw placement," Physics in Medicen & Biology, 2015, vol. 50, pp. 8007-8024, United Kingdom.

* cited by examiner

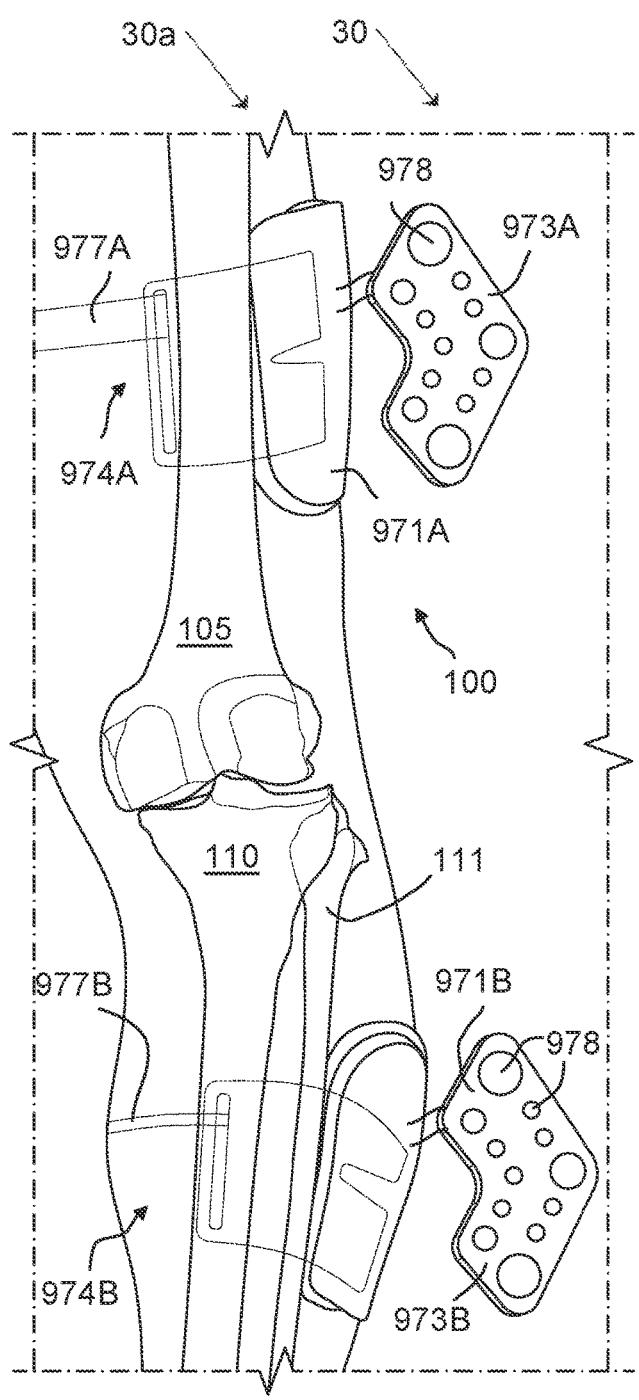
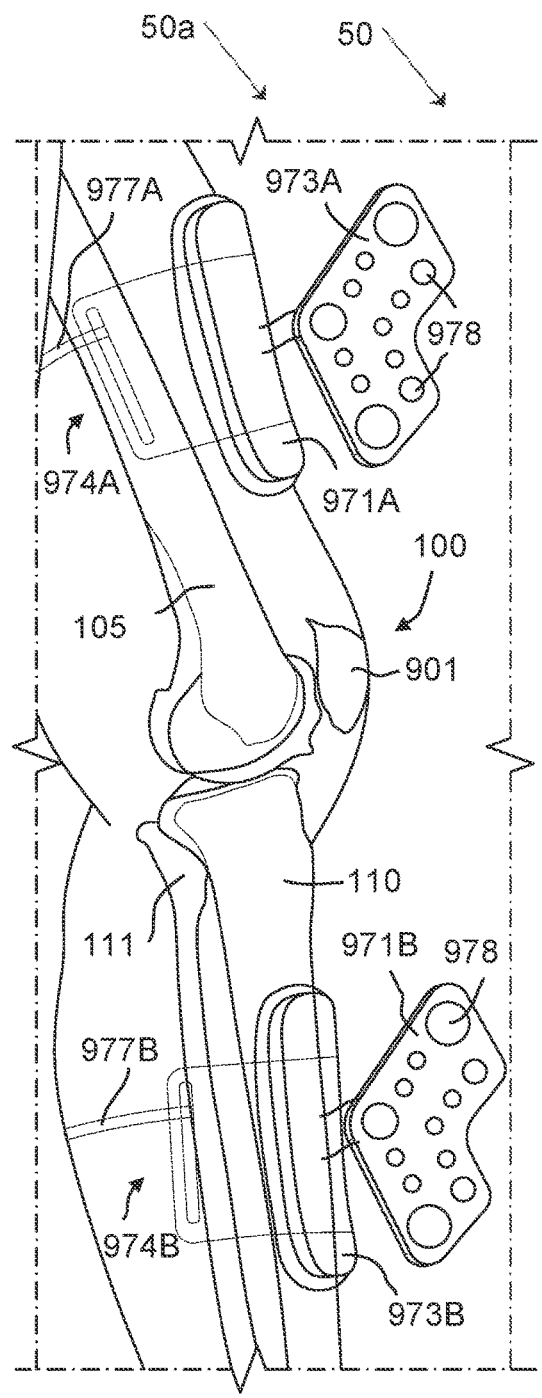
FIG. 9A
FIG. 9B

SYSTEMS AND METHODS OF USING THREE-DIMENSIONAL IMAGE RECONSTRUCTION TO AID IN ASSESSING BONE OR SOFT TISSUE ABERRATIONS FOR ORTHOPEDIC SURGERY

REFERENCE TO RELATED APPLICATION

This application claims the benefit of U.S. Provisional Application No. 63/217,567 filed on Jul. 1, 2021. The disclosure of this related application is hereby incorporated into this disclosure in its entirety.

BACKGROUND OF THE INVENTION

1. Technical Field

The present disclosure relates generally to the field of orthopedic joint replacement surgeries and more particularly to using photogrammetry and three-dimensional reconstruction techniques to aid surgeons and technicians in planning and executing orthopedic surgeries.

2. Related Art

An emerging objective of joint replacement surgeries is to restore the natural alignment and rotational axis or axes of the pre-diseased joint. However, this objective can be difficult to achieve in practice because joints comprise not only the articulating bones but also ancillary supporting bones and a variety of soft tissue, including cartilage, ligaments, muscle, and tendons. In the past, surgeons avoided restoring natural alignment altogether, or estimated alignment angles and other dimensions based on averages derived from a sample of the population. However, these averages often failed to account for natural variation in the anatomy of a specific patient, particularly when the patient suffered from chronic bone deforming diseases like osteoarthritis.

In an attempt to address this, some care providers started using computed tomography ("CT") scans and magnetic resonance imaging ("MR") techniques to survey patient's internal anatomy to help plan orthopedic surgeries. Data from these CT scans and MRIs have even been used to create three-dimensional ("3D") models in digital form. These models can be sent to professionals to design and produce patient-specific implants and instruments for said surgery. Additive manufacturing techniques (e.g., 3D printing) and other conventional production techniques can be used to construct physical implants or instruments that fit the patient's specific anatomy.

However, obtaining CT scans and MRIs can be complex, time consuming, and expensive. CT scans also tend to expose patients to higher levels of radiation per session than the patient might otherwise undergo using other non-invasive imaging techniques such as traditional radiography or ultrasounds. Moreover, scheduling considerations sometimes place the surveying CT scans or MRIs a month or more before the actual surgery. This delay can be exacerbated by the trend of gradually moving orthopedic surgical procedures to outpatient ambulatory surgical centers ("ASCs"). ASCs tend to be smaller facilities that often lack expensive on-site CT scanners and MRI machines. This often compels patients to schedule surveying appointments at hospitals.

Increased time between the surveying appointment and the surgery increases the risk that the patient's boney and soft tissue anatomy will further deteriorate or change under normal use or by the progression of a disease. Further deterioration may not only cause the patient additional discomfort, but it can also negatively affect the surveying data's usefulness to the surgical team. This can be especially problematic for patient-specific implants created from outdated data and for surgical techniques that seek to restore range of motion based on the natural alignment of pre-diseased joints. Furthermore, increased time between the pre-operative surveying appointment and the surgery increases the likelihood that extrinsic events will negatively affect the data. For example, an accident that dislocates or breaks a bone in the planned surgical area usually undermines the usefulness of the prior surveying data. Such risks may be higher in especially active or in especially frail individuals.

Additionally, not all patients have access to CT scans or MRIs for creating patient-specific implants or instruments. This can be due in part to the amount of time needed to acquire the data, send the data to a medical device design specialist, produce a 3D model of the desired anatomy, create a patient-specific instrument or implant design based upon the data or model, produce the patient-specific instrument or implant, track and ship said patient-specific instrument or implant to the surgical center, and sterilize said instrument or implant prior to the procedure. Lack of availability can also be a function of the patient's medical insurance and type of disease.

Knowing the precise amount of a patient's cartilage and bone loss can be useful in surgeries that seek to restore the natural range of motion of pre-diseased joints. Examples include primary knee replacement surgeries (typically called a "total knee arthroplasty" or "TKA"), total hip arthroplasties "THAs," and procedures that seek to alleviate the causes of femoroacetabular impingements ("FAI").

To use a knee joint and a TKA procedure as an example; a normal knee joint generally has a joint line (more specifically, a "flexion-extension ("FE") axis of rotation") that is generally about 2 degrees ("°") to 3° varus relative to the mechanical medial-lateral ("ML") line of the tibia. In an anatomic alignment TKA procedure, surgeons generally resect a portion of the patient's distal femoral condyles at about 3° valgus relative to the femur's ML line and then resect the tibia perpendicular to the longitudinal axis of the tibia, which results in a resection that is about 2° to 3° varus of the tibial ML line. The surgeon then places and tests components of the artificial joints over the resected area, evaluates the patient's range of motion, and then adjusts as needed.

However, every patient's physiology is slightly different. For this reason, and because of the extrinsic variabilities surrounding surveying data, many TKA surgeons opt for a more patient-specific kinematic alignment approach and use tools and procedures intended to locate the patient's pre-diseased joint line intraoperatively. These tools tend to measure the thickness of the hyaline articular cartilage of a non-worn, or lesser worn femoral condyle. Such tools tend to have a thickness gauge associated with the measurement end of the tool. The measurement end of the tool is usually inserted into the thickest area of cartilage on the lesser worn condyle until the tip of the measurement end reaches the underlying bone. The surgeon then uses the thickness gauge to measure and record the amount of remaining cartilage. The surgeon then uses this measurement as an approximation of the amount of cartilage wear on the worn condyle.

However, this technique has several limitations. Firstly, the lesser-worn condyle may have insufficient remaining cartilage from which to make an accurate measurement.

Secondly, even in cases where there is enough articular cartilage in the lesser-worn condyle, this cartilage measurement technique does not account for bone loss that occurs on the worn condyle. This problem can be compounded when there is little to no remaining cartilage on the adjacent condyle. As a result, existing intraoperative techniques cannot be used to reliably gauge the precise loss of both cartilage and bone in all kinematic alignment TKAs and therefore, these techniques, coupled with the problems and availability of accurate pre-operative data, can jeopardize the accurate alignment of the artificial joint line with the natural pre-diseased joint line. Repeated studies have shown that artificial joints that change the natural rotational axes of pre-diseased joints tend to contribute to poor function, pre-mature implant wear, and patient dissatisfaction.

SUMMARY OF THE INVENTION

Accordingly, there is a long felt but unresolved need to augment preoperative and intraoperative imaging technologies to accurately model bone aberrations and other physiology when planning and executing orthopedic surgeries.

The problems of limited access to conventional preoperative CT and MRI imaging techniques, data accuracy due to bone and cartilage deterioration between the time of preoperative imaging and surgical procedure, and the limitations of determining the natural joint lines of pre-diseased bones or joints that arise from using currently available intraoperative tools and techniques is mitigated by systems and/or methods for calculating the extent of a bone aberration comprising: using a deep learning network to identify an area of a bone aberration from an input of at least two separate two-dimensional ("2D") input images of a subject orthopedic element, wherein a first image of the at least two separate 2D input images is captured from a first transverse position, and wherein a second image of the at least two separate 2D input images is captures from a second transverse position offset from the first transverse position by an offset angle, and calculating a corrective area, wherein the corrective area removes the area of bone aberration.

It is contemplated that in certain exemplary embodiments, the first and second input images can be radiographic input images. Without being bound by theory, it is contemplated that radiographs can permit in-vivo analysis of the operative area and can account for external summation of passive soft tissue structures and dynamic forces occurring around the operative area, including the effect of ligamentous restraints, load-bearing forces, and muscle activity.

It is contemplated that certain embodiments in accordance with the present disclosure can be used to create patient-specific surgical plans, implants, and instruments from data derived from the cartilage and bony anatomy of the operative area, and/or data derived from the soft tissue structures of the operative area.

BRIEF DESCRIPTION OF THE DRAWINGS

The foregoing will be apparent from the following more particular description of exemplary embodiments of the disclosure, as illustrated in the accompanying drawings. The drawings are not necessarily to scale, with emphasis instead being placed upon illustrating the disclosed embodiments.

FIG. 9A is an image of subject orthopedic elements taken from the A-P position that shows an exemplary calibration jig.

FIG. 9B is an image of subject orthopedic elements of FIG. 8A taken from the M-L position that shows an exemplary calibration jig.

DETAILED DESCRIPTION OF THE PREFERRED EMBODIMENTS

Figure 1:
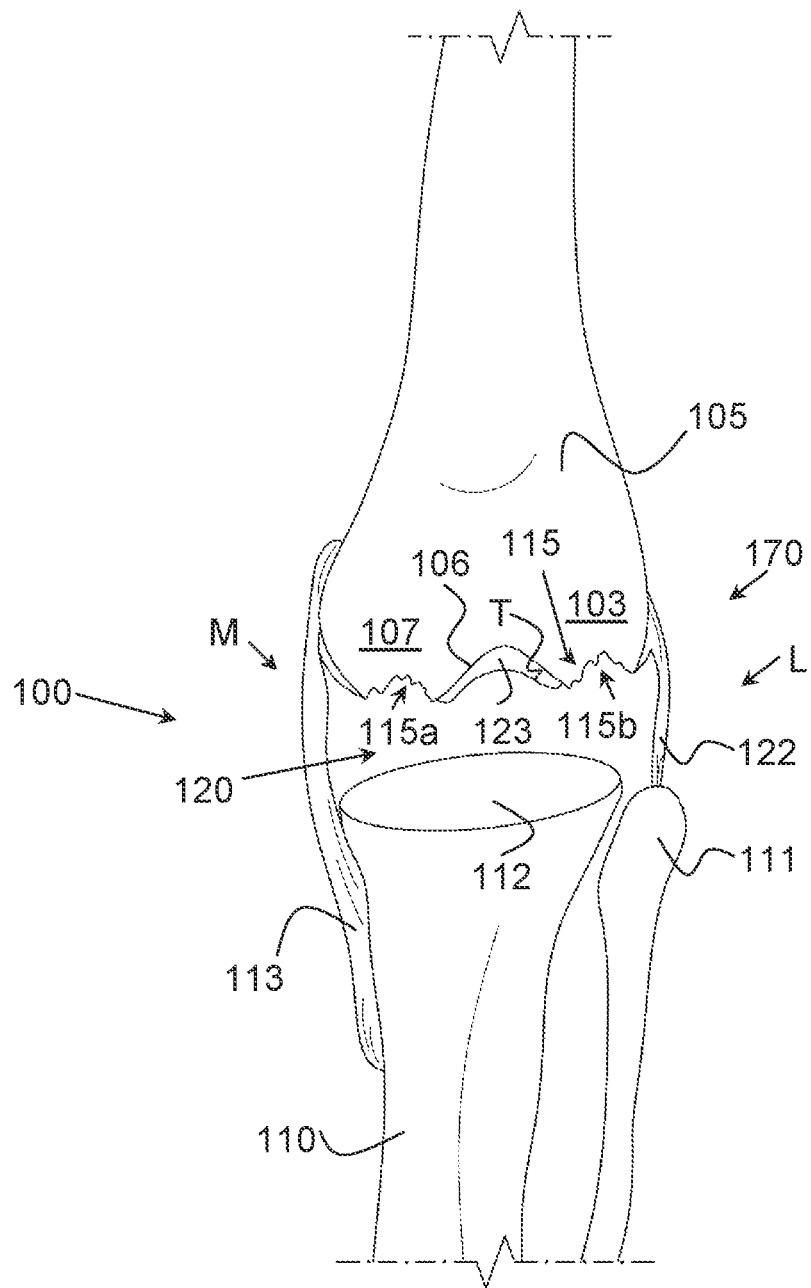
FIG. 1 is an anterior view of a simplified left knee joint depicting areas of negative bone aberration (i.e., bone loss) in the medial and lateral femoral condyles.

The following detailed description of the preferred embodiments is presented only for illustrative and descriptive purposes and is not intended to be exhaustive or to limit the scope and spirit of the invention. The embodiments were selected and described to best explain the principles of the invention and its practical application. One of ordinary skill in the art will recognize that many variations can be made to the invention disclosed in this specification without departing from the scope and spirit of the invention.

Similar reference characters indicate corresponding parts throughout the several views unless otherwise stated. Although the drawings represent embodiments of various features and components according to the present disclosure, the drawings are not necessarily to scale and certain features may be exaggerated to better illustrate embodiments of the present disclosure, and such exemplifications are not to be construed as limiting the scope of the present disclosure.

Except as otherwise expressly stated herein, the following rules of interpretation apply to this specification: (a) all words used herein shall be construed to be of such gender or number (singular or plural) as such circumstances require; (b) the singular terms "a," "an," and "the," as used in the specification and the appended claims include plural references unless the context clearly dictates otherwise; (c) the antecedent term "about" applied to a recited range or value denotes an approximation with the deviation in the range or values known or expected in the art from the measurements; (d) the words, "herein," "hereby," "hereto," "hereinbefore," and "hereinafter," and words of similar import, refer to this specification in its entirety and not to any particular paragraph, claim, or other subdivision, unless otherwise specified; (e) descriptive headings are for convenience only and shall not control or affect the meaning of construction of part of the specification; and (f) "or" and "any" are not exclusive and "include" and "including" are not limiting. Further, the terms, "comprising," "having," "including," and "containing" are to be construed as open-ended terms (i.e., meaning "including but not limited to").

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether explicitly described.

To the extent necessary to provide descriptive support, the subject matter and/or text of the appended claims are incorporated herein by reference in their entirety.

Recitation of ranges of values herein are merely intended to serve as a shorthand method of referring individually to each separate value falling within the range of any subranges there between, unless otherwise clearly indicated herein. Each separate value within a recited range is incorporated into the specification or claims as if each separate value were individually recited herein. Where a specific range of values is provided, it is understood that each intervening value, to the tenth or less of the unit of the lower limit between the upper and lower limit of that range and any other stated or intervening value in that stated range of sub range thereof, is included herein unless the context clearly dictates otherwise. All subranges are also included. The upper and lower limits of these smaller ranges are also included therein, subject to any specifically and expressly excluded limit in the stated range.

It should be noted that some of the terms used herein are relative terms. For example, the terms, "upper" and, "lower" are relative to each other in location, i.e., an upper component is located at a higher elevation than a lower component in each orientation, but these terms can change if the orientation is flipped. The terms, "inlet" and "outlet" are relative to the fluid flowing through them with respect to a given structure, e.g., a fluid flows through the inlet into the structure and then flows through the outlet out of the structure. The terms, "upstream" and "downstream" are relative to the direction in which a fluid flows through various components prior to flowing through the downstream component.

The terms, "horizontal" and "vertical" are used to indicate direction relative to an absolute reference, i.e., ground level. However, these terms should not be construed to require structure to be absolutely parallel or absolutely perpendicular to each other. For example, a first vertical structure and a second vertical structure are not necessarily parallel to each other. The terms, "top" and "bottom" or "base" are used to refer to locations or surfaces where the top is always higher than the bottom or base relative to an absolute reference, i.e., the surface of the Earth. The terms, "upwards" and "downwards" are also relative to an absolute reference; an upwards flow is always against the gravity of the Earth.

Throughout this disclosure, various positional terms, such as "distal," "proximal," "medial," "lateral," "anterior," and "posterior," will be used in the customary manner when referring to the human anatomy. More specifically, "distal" refers to the area away from the point of attachment to the body, while "proximal" refers to the area near the point of attachment to the body. For example, the distal femur refers to the portion of the femur near the tibia, whereas the proximal femur refers to the portion of the femur near the hip. The terms, "medial" and "lateral" are also essentially opposites. "Medial" refers to something that is disposed closer to the middle of the body. "Lateral" means that something is disposed closer to the right side or the left side of the body than to the middle of the body. Regarding, "anterior" and "posterior," "anterior" refers to something disposed closer to the front of the body, whereas "posterior" refers to something disposed closer to the rear of the body."

"Varus" and "valgus" are broad terms and include without limitation, rotational movement in a medial and/or lateral direction relative to the knee joint.

It will be appreciated that the term "bone aberration" as used herein can refer to an area of external or internal bone loss, an area of abnormal excess bone (such as in an osteophyte (i.e., "bone spur"), or any other area of bone that is discontiguous with the natural area of the surrounding bone.

All methods for identifying an area of bone aberration for the purpose of calculating a corrective area, wherein the corrective area removes the area of bone aberration relative to a surrounding bone area are considered to be within the scope of this disclosure. By way of example, the below section describes exemplary embodiments of systems and methods used to restore the natural joint line and rotational axes of a pre-diseased knee joint in a total knee arthroplasty ("TKA").

To describe a primary TKA generally: the surgeon typically initiates the surgical procedure by making a generally vertical medial parapatellar incision on the anterior or anteromedial side of the operative knee. The surgeon continues to incise the fatty tissue to expose the joint capsule. The surgeon may then perform a medial parapatellar arthrotomy to pierce the joint capsule. A retractor may then be used to move the patella generally laterally to expose the distal condyles of the femur (see 103 and 107, FIG. 1) and the cartilaginous meniscus resting on the proximal tibial plateau (see generally 112, FIG. 1). The surgeon then removes the meniscus and uses instrumentation to measure and resect the distal femur 105 and proximal tibia 110 to accommodate trial implants. Trial implants are test endoprostheses that generally have the same functional dimensions of the actual endoprostheses, but trial implants are designed to be temporarily installed and removed for the purposes of evaluating the fit of the actual endoprostheses and for the purposes of evaluating the knee joint's kinematics. The trial implants and the actual endoprosthetic implants are generally disposed adjacent to these resections once installed. Therefore, the position and orientation of these femoral and tibial resections largely dictates the orientation of the trial and actual endoprosthetic implants and thereby the position and orientation of the reconstructed joint line.

This tibial resection is then preformed. Once resected, the resected area of the tibia can be known as the "tibial plateau." Next, the surgeon may place a trial tibial component on the resected proximal tibial plateau. The surgeon generally uses different instrumentation to measure and resect the distal femoral condyles for the purpose of installing a trial femoral component. If the trial components are not seated appropriately, the surgeon my use further instrumentation to measure and resect the femoral condyles and/or the tibial plateau until the desired seating is achieved.

The surgeon then generally inserts a trial meniscal insert between the trial tibial tray and the trial femoral component to test the knee's flexion and extension, general stability, and patellar tracking on the trial implants. Once satisfied with the trial and movement characteristics, the surgeon can use bone cement to permanently affix the actual tibial and femoral components of the endoprosthetic implant or use a press-fit implant and avoid use of bone cement if desired.

Figure 6:
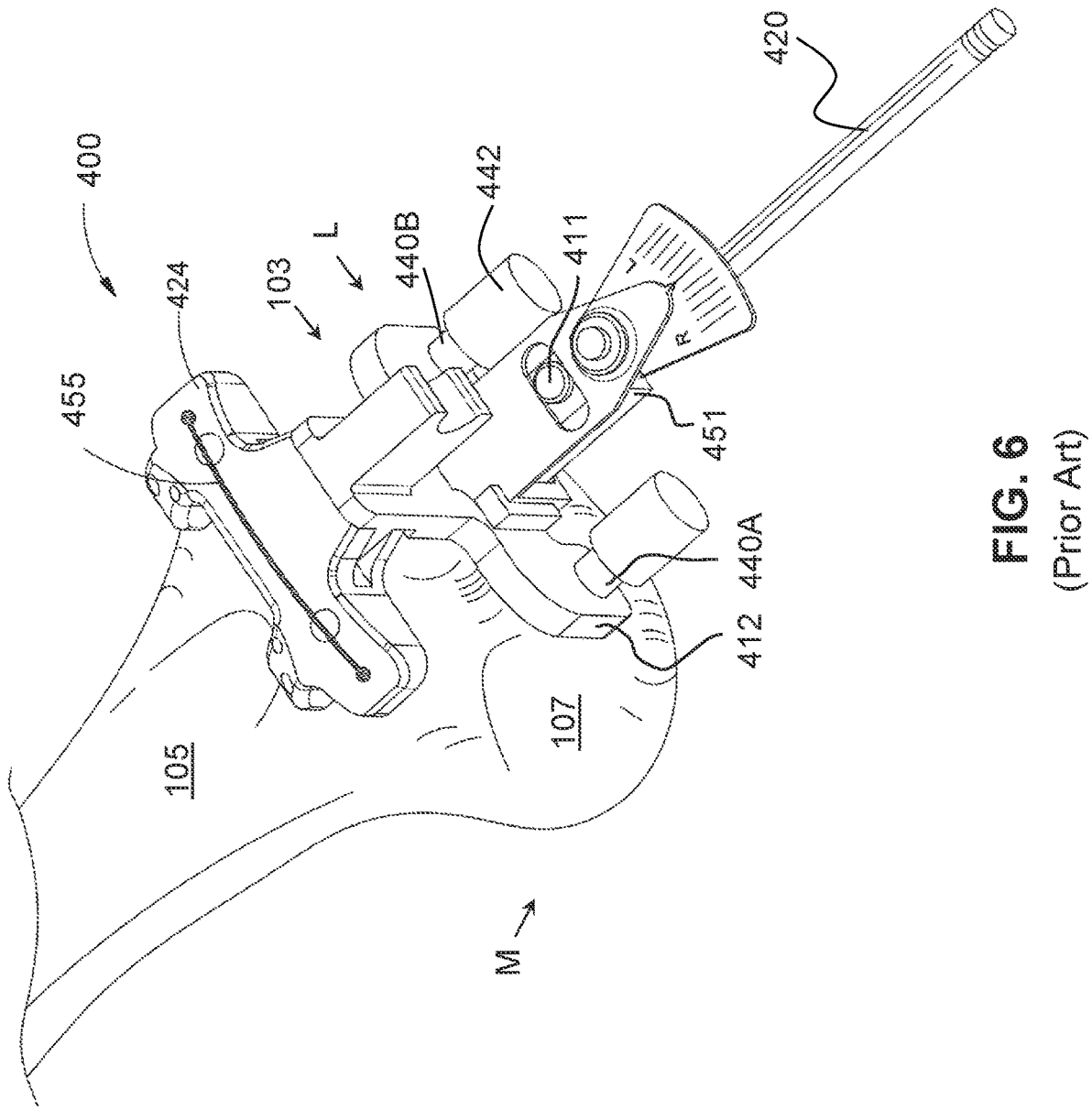
FIG. 6 is a perspective view of a femoral resection guide attached to a femoral resection guide positioning instrument.

The newest alignment school of thought is the kinematic alignment philosophy. The kinematic alignment philosophy recognizes that every patient's physiology is slightly different and seeks to restore the patient's natural pre-diseased joint line by taking actual measurements of the operative physiology to ascertain the position of the native joint line. Once these measurements are known, tooling, such as pivoting femoral resection guide locator 400 (FIGS. 2, 4 and 6) or resection guides 424 (FIG. 6) are then placed onto the exposed bones. Resection guides 424 may be custom made to complement the exposed bone or the resection guides 424 can selectively lock into a femoral resection guide locator 400. These femoral resection guide locators 400 can have adjustable positioning mechanisms (see 440) with which the surgeon can adjust the orientation of the resection guide 424 relative to the exposed bone based on the patient's specific measurements. Once the resection guide 424 is set at the desired orientation, the resection guide 424 is then temporarily affixed to the bone. The surgeon then inserts a surgical saw through a resection slot 455 of the oriented resection guide 424 to resect the undying bone in the desired resection plane. Because the position and orientation of the femoral and tibial resections largely dictate the orientation of the trial and actual endoprosthetic implants, the position and the orientation of the resection guide 424 largely determines position and orientation of the reconstructed joint axes of rotation.

Although it is contemplated that the methods and systems described herein may be especially useful for kinematic alignment, nothing in this disclosure limits the use of the systems and methods described herein to kinematic alignment. By way of example, the systems and methods described herein may be used with anatomic alignment, mechanical alignment, or any other alignment method provided that a present bone aberration would affect the positioning of the alignment instruments (see the resection guide locator 400 and the alignment guide 600). Furthermore, nothing in this disclosure limits the exemplary systems and methods described herein to use on the knee joint. Any orthopedic procedure in which would be desirable for the surgeon to have pre- or intraoperative knowledge of a bone or soft tissue aberration are considered to be within the scope of this disclosure. Examples of such orthopedic procedures include but are not limited to hip arthroplasties, and procedures that seek to alleviate the causes of femoroacetabular impingements.

FIG. 1 is an anterior view of a simplified left knee joint (i.e., an example collection of subject orthopedic elements 100 in an example operative area 170). The examples described with reference to FIGS. 1-5 relate to an exemplary knee joint for illustration purposes. It will be appreciated that the "orthopedic element" 100 referenced throughout this disclosure is not limited to the anatomy of a knee joint, but can include any skeletal structure and associated soft tissue, such as tendons, ligaments, cartilage, and muscle. A non-limiting list of example orthopedic elements 100 includes any partial or complete bone from a body, including but not limited to a femur, a tibia, a pelvis, a vertebra, a humerus, an ulna, a radius, a scapula, a skull, a fibula, a clavicle, a mandible, a rib, a carpal, a metacarpal, a metatarsal, a phalange, or any associated tendon, ligament, skin, cartilage, or muscle. It will be appreciated that an example operative area 170 can comprise several subject orthopedic elements 100.

The example orthopedic elements 100 depicted in FIG. 1 are the distal aspect of the femur 105, the proximal aspect of the tibia 110, the proximal aspect of the fibula 11, the medial collateral ligament ("MCL") 113, the lateral collateral ligament ("LCL") 122, and articular cartilage 123 disposed over the femoral distal condyles 107, 103. Areas of bone aberration (generally 115) are shown on the femoral distal condyles 107, 103. A medial area of bone aberration 115a is shown in the medial condyle 107 and a lateral area of bone aberration 115b is shown in the lateral condyle 103 of the femur 105 (collectively, "distal femoral condyles"). In FIG. 1, the areas of bone aberration 115a, 115b are "negative bone aberrations," i.e., areas of bone loss. FIG. 1 depicts the medial condyle 107 and the lateral condyle 103 of the distal aspect of the femur 105 disposed over the tibial plateau 112 of the proximal aspect of the tibia 110. The MCL 113 engages the distal femur 105 to the proximal tibia 110 on the medial side M. Likewise, the LCL 122 engages the distal femur 105 to the fibula 111 on the lateral side L. A femorotibial gap 120 separates the distal femur 105 from the tibial plateau 112. Hyaline articular cartilage 123 is shown around the areas of bone aberration 115a, 115b on the distal femur 105.

The position of the native pre-diseased joint line is largely set by the interaction between the soft tissue (e.g., articular cartilage 123) on femoral condyles 107, 103 and the meniscus as supported by the underlying bone (e.g., the tibia 110). In the absence of an area of bone aberration 115a, 115b (e.g., the area of bone loss depicted in FIG. 1), knowing the thickness of the pre-diseased cartilage 123 can be used to closely approximate the location of the pre-diseased joint line.

Figure 7:
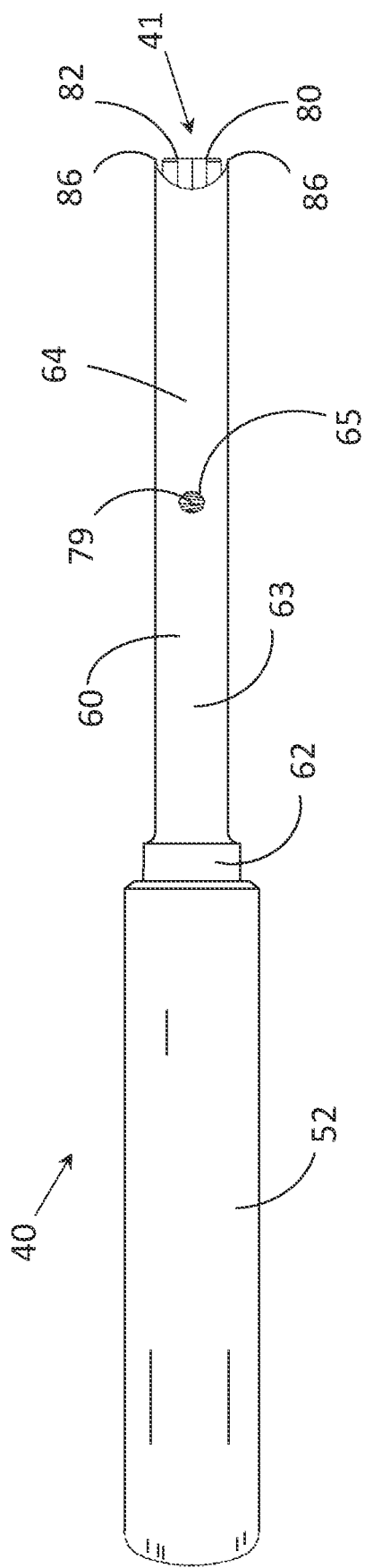
FIG. 7 is a side view of a cartilage thickness gauge.

FIG. 7 depicts an example cartilage thickness gauge 40. The depicted thickness gauge 40 comprises an elongated handle portion 52, which a surgeon can use to hold and manipulate the instrument. A shoulder 62 engages a shaft portion 60 to the handle portion 52. The shaft portion 60 comprises a proximal solid portion 63 and a distal hollow portion 64. The hollow portion 64 extends to the measurement end 41. The hollow portion 64 receives a piston 80. The piston 80 is disposed within the hollow portion 64 and biased against a spring 79 disposed between the piston 80 and the solid portion 63 of the shaft portion 60. Markers (not depicted) on the piston 80 may be visible through a viewing portal in the shaft portion 60. These markers are desirably disposed at regular increments, such as 1 millimeter ("mm") increments. A reference line may be disposed adjacent to the viewing portal. Likewise, the markers that are visible through the viewing portal move relative to the reference line.

All methods for assessing cartilage wear are considered to be within the scope of this disclosure. One example method of using this example cartilage thickness gauge 40 (FIG. 7) and resection guides to perform a kinematic alignment technique is further described in U.S. patent application Ser. No. 16/258,340. The entirety of U.S. patent application Ser. No. 16/258,340 is incorporated herein by reference. The method disclosed in this application uses a cartilage thickness gauge 40 to measure the thickness T (FIG. 1) of the hyaline articular cartilage 123 (FIG. 1) that is adjacent to a non-worn, or lesser worn femoral condyle (i.e., either 107 or 103). The measurement end 41 of the cartilage thickness gauge 40 is inserted into the thickest area of cartilage 123 adjacent the lesser worn condyle until the tips 86 of the measurement end 41 reaches the underlying bone 106 (FIG. 1). In this manner, pressing the tips 86 of the measurement end 41 into the thickest area of remaining proximal cartilage 123 causes the piston 80 to compress the spring 79. At the same time, the markers on the piston 80 move relative to the reference line and are visible through the viewing portal to thereby indicate the thickness of the cartilage 123 disposed under the measurement end 41. The surgeon then records the amount of remaining cartilage (i.e., the cartilage thickness T) and uses this measurement as an approximation of the amount of cartilage wear on the worn condyle. This process is desirably repeated for each distal femoral condyle 103, 107 and each posterior femoral condyle (107a, 103a, FIG. 5).

By way of a different example for evaluating the thickness of the cartilage 123, a surgeon or technician may use an intra-operative probe to map the location and physical properties of the soft tissue, such as the soft tissue's elasticity and density. A system can use this data to calculate an amount of cartilage wear over the condyles.

Figure 2:
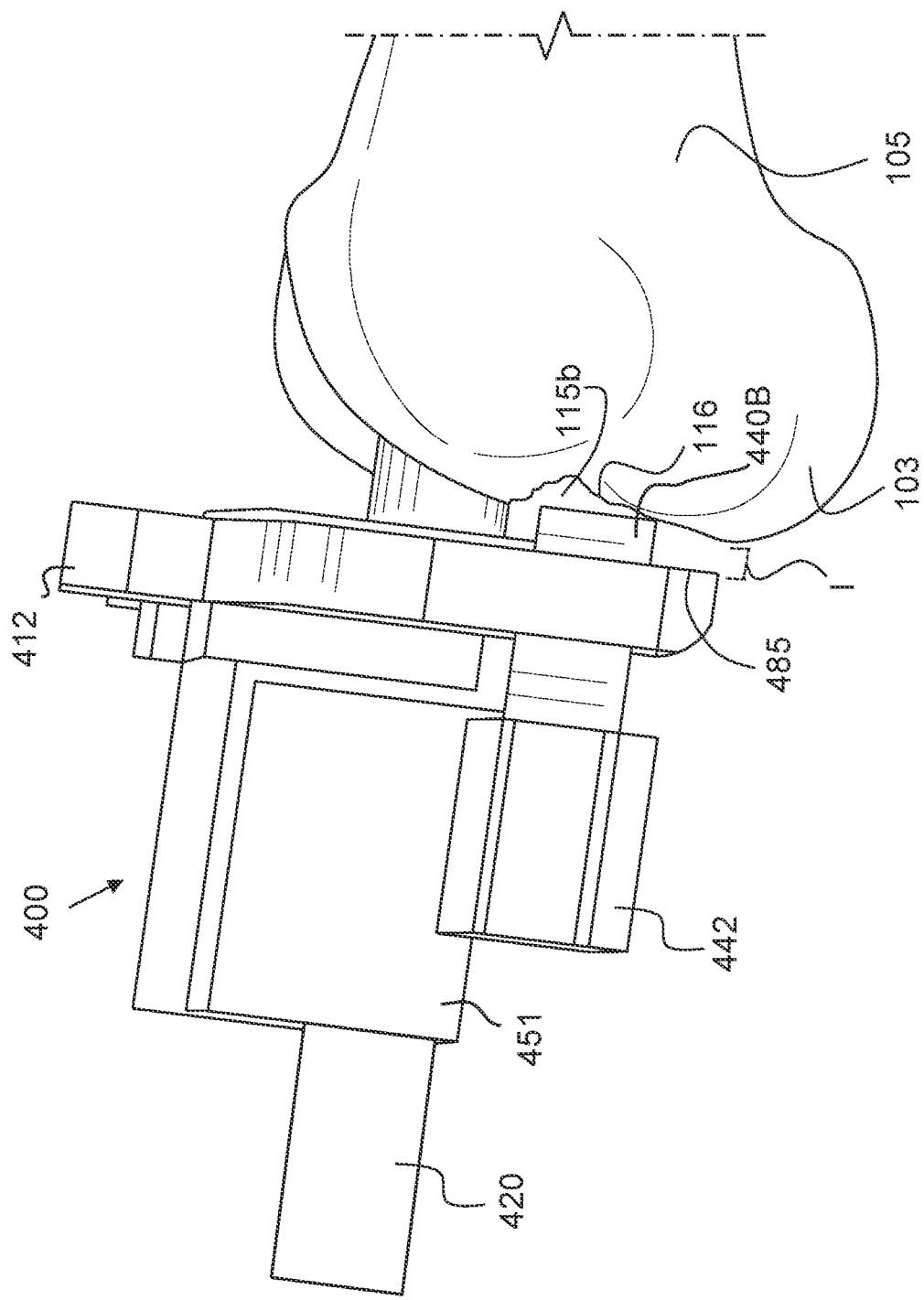
FIG. 2 is a side view of a femoral resection guide positioning instrument having an adjustment pad extending through the negative bone aberration to be disposed on an exposed surface of worn bone on the lateral femoral condyle.

Referring now to FIG. 2, at any time after the exposure of the distal femur 105, the surgeon may drill an intramedullary canal down roughly the center of the distal femur 105, and then place an intramedullary rod 420 (see also FIG. 6) into the evacuated intramedullary canal to provide a foundation for selectively disposing referencing instrumentation relative to the distal femur 105. Once the intramedullary rod 420 is securely seated, a stable portion 451 of the pivoting femoral resection guide locator 400 can be slid onto the intramedullary rod 420 such that adjustment pads 440A, 440B are disposed adjacent to the medial distal femoral condyle 107 and lateral distal femoral condyle 103 respectively.

The stable portion 451 can be an intramedullary rod holder member, or other device configured to be secured to a fixed position relative to a pivoting body portion 412. The body portion 412 is configured to pivot relative to the stable portion 451. A pin 411 (FIG. 6) may be closely fitted to and disposed in aligned annular holes in the stable portion 451 and the body portion 412 respectively and in this manner, the body portion 412 of the pivoting femoral resection guide locator 400 can be said to "configured to pivot" relative to the stable portion 451, or be said to be in a "pivoting relationship" with the stable portion 451.

The adjustment pads 440A, 440B (FIG. 6) are then extended from the distal reference surface 485 of the resection guide locator 400 to touch the femoral condyles 103, 107. The length l of each adjustment pad 440 relative to the reference surface 485 is desirably the same length l as the measurement of the thickness T of the associated adjacent hyaline articular cartilage 123 for each condyle.

For example, if there is 2 mm of cartilage wear on the medial side M and 0 mm on the lateral side L, the surgeon will extend the medial adjustment pad 440A 2 mm. The surgeon then places each adjustment pad 440 on the appropriate condyle. In this example, the lateral adjustment pad 440B would remain nearly flush with the distal reference surface 485. The position of the distal reference surface 485 relative to the intramedullary rod 420 thereby sets the resection angle. The resection guide 424 (FIG. 6) is then pinned to the femur 105 at the desired cutting angle, the femoral resection guide locator 400 is removed, and the surgeon resects the distal femoral condyles 103, 107 through the resection slot 455 at the desired resection angle.

However, these adjustments only account for cartilage wear present. The adjustments do not account for areas of bone aberrations 115a, 115b such as bone loss that can occur on the worn condyle (e.g., the lateral condyle 103, or the medial condyle 107). The adjustment pads 440A, 440B are typically set based on the measurement of the cartilage thickness gauge 40. If a patient suffers from significant bone loss, of if significant osteophytes (commonly referred to as "bone spurs") are present, the position of distal reference surface 485 of the femoral resection guide locator 400 will not be disposed at the precise location of the pre-diseased articular surface. Moreover, if the surgeon extends the adjustment pad 440 to the remaining area of bone (as depicted in FIG. 2), it is not possible to know with precision where the pre-diseased bone ended and where the articular cartilage 123 began. As such, even if the amount of cartilage wear can be reasonably approximated by measuring the thickest area of adjacent, unworn cartilage 123, it is not possible to precisely know the depth of the missing bone. As such, any adjustment of the adjustment pad 440 to touch a condyle having areas of significant bone loss (and by extension, any adjustment of the position of the distal reference surface 485 and resection guide 424) is at best an approximation of the pre-diseased articular surface. Lacking precision in this area risks miscalculating the orientation of the natural pre-diseased rotational axis of the joint. As such, any estimation error can negatively affect patient comfort and the useful life of the implant.

As a result, using the pivoting femoral resection guide locator 400 described in U.S. patent application Ser. No. 16/258,340 and existing intraoperative techniques cannot be used to reliably gauge the precise loss of both cartilage and bone in all TKAs and therefore, these techniques, coupled with the problems and availability of accurate pre-operative data, can undermine accurate reconstruction of an artificial joint line with the natural pre-diseased joint line.

To illustrate this, FIG. 2 shows a side view of a femoral resection guide locator 400 having an adjustment pad 440B extending through a negative area of bone aberration 115b to be disposed on an exposed surface of worn bone 116 on the lateral condyle 103. The extended length l of the pad adjuster 440 relative to the distal reference surface 485 is initially set by the measurement of the cartilage thickness (see 123), which may be obtained using the cartilage thickness gauge 40 as described above, or by other cartilage thickness measurement methods. However, with femoral condyles 103, 107 that suffer from bone loss, it was not previously possible to ascertain the amount of bone aberration (e.g., bone loss in this instance) with certainty using a femoral resection guide locator 400 with pad adjusters 440A, 440B.

For example, the precise depth of the negative bone aberration (i.e., bone loss) on the lateral condyle 103 is not easily ascertainable using conventional methods. Improperly accounting for the depth of the negative bone aberration risks misalignment of the pivoting femoral resection guide locator 400 because extending the pad adjuster 440B to the value of the measured cartilage thickness and placing the end of the pad adjuster 440B on the exposed surface of the worn bone 116 is now no longer indicative of the pre-diseased articular surface. That is, if the surgeon initially sets the extended length l of the depicted pad adjuster 440B to 2 mm from the distal reference surface 485 (per the cartilage gauge measurement), and then disposes the pad adjuster 440 such that the pad adjuster 440 contacts the exposed surface of the worn bone 116, the pad adjuster would extend into the area of bone loss 115b by the unknown depth of the negative bone aberration 115b, thereby changing the angle of the distal reference surface 485 (and by extension, the cutting surface) relative to the intramedullary rod 420. This new cutting angle is not reflective of the pre-diseased articular surface and therefore would not be useful to align the knee kinematically.

The surgeon may attempt to compensate by adding length (see 1) to the pad adjuster 440 to try to estimate the depth of bone loss, but the precise amount of loss is unknown to the surgeon. Therefore, the surgeon may over or under-estimate the amount of loss, thereby also risking misalignment of the femoral resection guide locator 400 relative to the actual articular surface of the pre-diseased joint. Kinematic alignment is a femoral articular surface referencing technique. Therefore, mistakes made when referencing the articular surface will be transferred to the proximal tibia if not corrected, thereby potentially further exacerbating the initial error. Further, as FIG. 2 illustrates, the area of bone aberration 115b, and the exposed surface of the worn bone 116 may not be uniform in depth. This can undermine the initial stability of the resection guide locator's angled position relative to the intramedullary rod 420.

In recent years, it has become possible to use multiple 2D images, such as X-ray radiographs from an imaging system, to create 3D models of an operative area 170. These models can be used pre-operatively to plan surgeries much closer to the date of the actual surgery. Moreover, these 3D models can be generated intraoperatively to check against the pre-operative model and plan, or these 3D models can function as the native model from which areas of bone aberration can be calculated. However, X-ray radiographs have typically not been used as inputs for 3D models previously because of concerns about image resolution and accuracy. X-ray radiographs are 2D representations of 3D space. As such, a 2D X-ray radiograph necessarily distorts the image subject relative to the actual object that exists in three dimensions. Furthermore, the object through which the X-ray passes can deflects the path of the X-ray as it travels from the X-ray source (typically the anode of the X-ray machine) to the X-ray detector (which may include by non-limiting example, X-ray image intensifiers, phosphorus materials, flat panel detectors "FPD" (including indirect conversion FPDs and direct conversion FPDs), or any number of digital or analog X-ray sensors or X-ray film). Defects in the X-ray machine itself or in its calibration can also undermine the usefulness of X-ray photogrammetry and 3D model reconstruction. Additionally, emitted X-ray photons have different energies. As the X-rays interact with the matter placed between the X-ray source and the detector, noise and artifacts can be produced in part because of Compton and Rayleigh scattering, the photoelectric effect, extrinsic variables in the environment or intrinsic variables in the X-ray generation unit, X-ray detector, and/or processing units or displays.

Moreover, in a single 2D image, the 3D data of the actual subject is lost. As such, there is no data that a computer can use from a single 2D image to reconstruct a 3D model of the actual 3D object. For this reason, CT scans, MRIs, and other imaging technologies that preserve third dimensional data were often preferred inputs for reconstructing models of one or more subject orthopedic elements (i.e., reconstructing a 3D model from actual 3D data generally resulted in more accurate, higher resolution models). However, certain exemplary embodiments of the present disclosure that are discussed below overcome these issues by using deep learning networks to improve the accuracy of reconstructed 3D models generated from X-ray photogrammetry and to identify areas of bone aberration on or in the reconstrued 3D model. In certain exemplary embodiments, the areas of bone aberration can be corrected or eliminated using curve fitting algorithms (i.e., an example surface adjustment algorithm).

An exemplary method for calculating the extent of a bone aberration can comprise: generating a 3D model of an operative area 170 from at least two 2D images, wherein a first image is captured at a first transverse position, wherein a second image is captured at a second transverse position, and wherein the first transverse position is different than the second transverse position, identifying an area of a bone aberration on the 3D model, and calculating a corrective area, wherein the corrective area removes the area of bone aberration from the 3D model (i.e., relative to a surrounding bone area).

An exemplary system for calculating the extent of a bone aberration can comprise: a radiographic imaging machine 1800 comprising an emitter 21 and a detector 33 (FIG. 18), wherein the detector 33 of the radiographic imaging machine 1800 captures a first image 30 (FIGS. 9 and 10) in a first transversion position 30a (FIGS. 9 and 10) and a second image 50 (FIGS. 9 and 10) in a second transverse position 50a (FIGS. 9 and 10), wherein the first transverse position 30a is offset from the second transverse position 50a by an offset angle θ (FIG. 10), a transmitter 29 (FIG. 18), and a computational machine 1600 wherein the transmitter 29 transmits the first image 30 and the second image 50 from the detector 33 to the computational machine 1600, and wherein the computational machine 1600 is configured to identify an area of a bone aberration 115 on the 3D model of the subject orthopedic element 1100, and calculate a corrective area, wherein the corrective area removes the area of bone aberration from the 3D model of the subject orthopedic element 1100 (i.e., relative to a surrounding bone area).

In certain exemplary embodiments, an exemplary system may further comprise a display 19.

In certain exemplary embodiments, an exemplary system may further comprise a manufacturing machine 18. In exemplary embodiment comprising a manufacturing machine 18, the manufacturing machine 18 can be an additive manufacturing machine. In such embodiments, the additive manufacturing machine may be used to manufacture the 3D model of the subject orthopedic element 1100 or the 3D model of the bone aberration 115*m*.

Although X-ray radiographs from an X-ray imaging system may be desirable because X-ray radiographs are relatively inexpensive compared to CT radiographs and because the equipment for some X-ray imaging systems, such as a fluoroscopy system, are generally sufficiently compact to be used intraoperatively, nothing in this disclosure limits the use of the 2D images to X-ray radiographs unless otherwise expressly claimed, nor does anything in this disclosure limit the type of imaging system to an X-ray imaging system. Other 2D images can include by way of example: CT-images, CT-fluoroscopy images, fluoroscopy images, ultrasound images, positron emission tomography ("PET") images, and MRI images. Other imaging systems can include by way of example: CT, CT-fluoroscopy, fluoroscopy, ultrasound, PET, and MRI systems.

Preferably, the exemplary methods can be implemented on a computer platform (e.g., a computational machine 1600) having hardware such as one or more central processing units (CPU), a random access memory (RAM), and input/output (I/O) interface(s). An example of the architecture for an example computational machine 1600 is provided below with reference to FIG. 16.

In certain exemplary embodiments, the 3D model of the subject orthopedic element 1100 and/or the 3D model of the bone aberration 115*m* can be a computer model. In other exemplary embodiments, the 3D model of the subject orthopedic element 1100 and/or the 3D model of the bone aberration 115*m* can be a physical model.

There are a variety of methods to generate a 3D model from 2D preoperative or intraoperative images. By way of example, one such method may comprise receiving a set of 2D radiographic images of an operative area 170 of a patient with a radiographic imaging system, computing a first 3D model using epipolar geometry principles with a coordinate system of the radiographic imaging system and projective geometry data from the respective 2D images (see FIGS. 9 and 10). Such an exemplary method may further comprise projecting the first 3D model on the 2D radiographic images and then adjusting the initial 3D model by registering the first and second radiographic images 30, 50 on the first 3D model with an image-to-image registration technique. Once the image-to-image registration technique has been applied, a revised 3D model may be generated. This process can repeat until the desired clarity in achieved.

By way of another example, a deep learning network (also known as a "deep neural network" ("DNN"), such as a convolutional neural network ("CNN"), recurrent neural network ("RNN"), modular neural network, or sequence to sequence model, can be used to generate a 3D model of the subject orthopedic element 1100 and/or a 3D model of the bone aberration 115*m* from a set of at least two 2D images of an operative area 170 of a patient and to identify areas of bone aberrations 115. The 2D images are desirably tissue penetrating images, such as radiographic images (e.g., X-ray or fluoroscopy images). In such a method, the deep learning network can generate a model from the projective geometry data (i.e., spatial data 43 or volume data 75) from the respective 2D images. The deep learning network can have the advantage of being able to generate a mask of the different subject orthopedic elements 100 (e.g., bones) or bone aberrations 115 in the operative area 170 as well as being able to calculate a volume (see 61, FIG. 11) of one or more imaged orthopedic elements 100.

Figure 8:
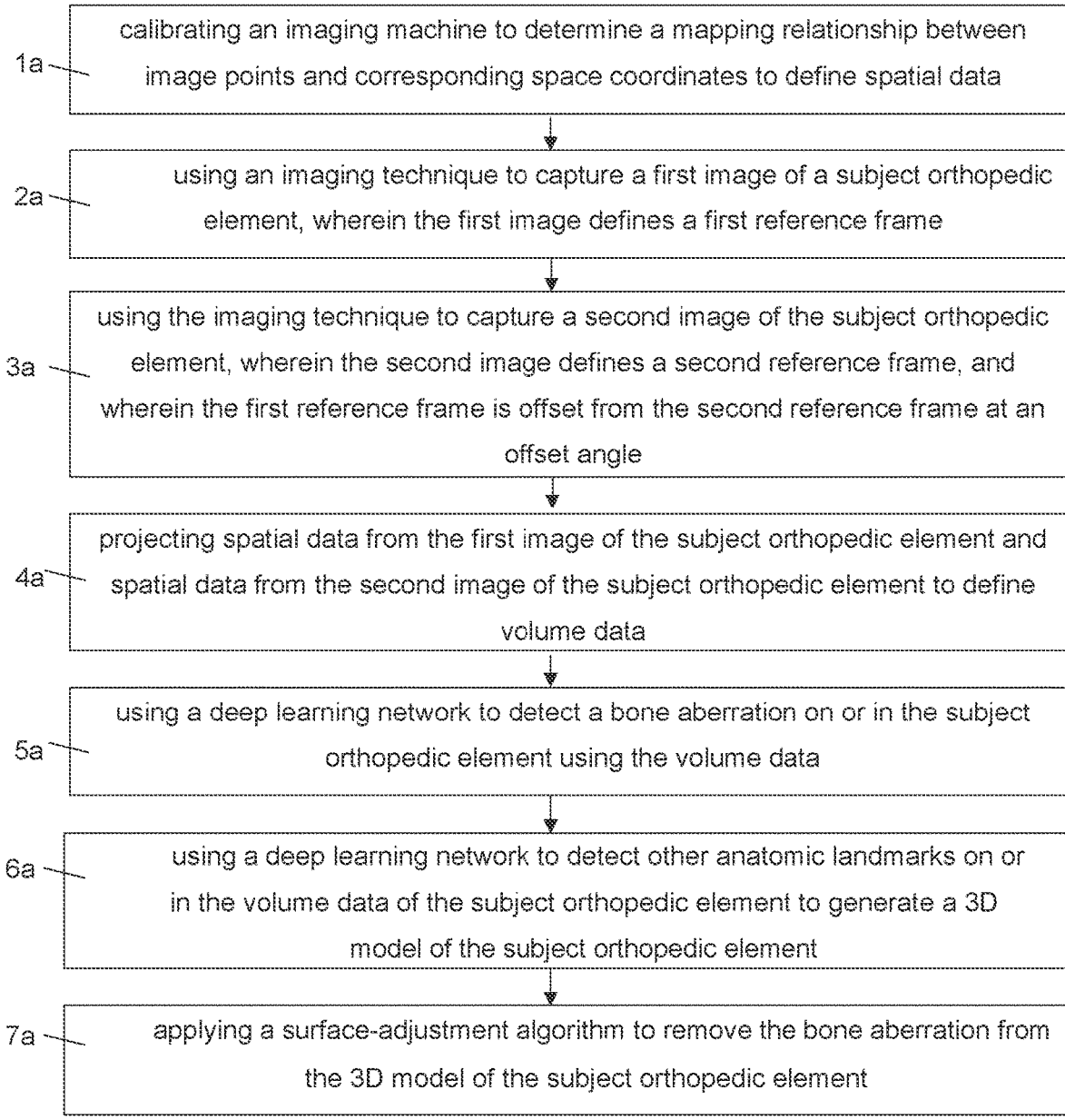
FIG. 8 is a flow chart depicting the steps of an exemplary method.

FIG. 8 is a flow chart that outlines the steps of an exemplary method that uses a deep learning network to identify an area of bone aberration 115 on or in an imaged orthopedic element 100 using two flattened input images (30, 50, FIGS. 9 and 10) taken from an offset angle θ. The exemplary method comprises: step 1*a* calibrating an imaging machine 1800 (FIG. 18) to determine a mapping relationship between image points (see $X_L$, $e_L$, $X_R$, $e_R$, FIG. 10) and corresponding space coordinates (e.g., Cartesian coordinates on an x, y plane) to define spatial data 43. The imaging machine 1800 is desirably a radiographic imaging machine capable of producing X-ray images ("X-ray images" can be understood to include fluoroscopic images), but all medical imaging machines are considered to be within the scope of this disclosure.

Step 2*a* comprises capturing a first image 30 (FIG. 9) of a subject orthopedic element 100 using the imaging technique (e.g., an X-ray imaging technique, a CT imaging technique, an MRI imaging technique, or an ultrasound imaging technique), wherein the first image 30 defines a first reference frame 30*a*. In step 3*a*, a second image 50 (FIG. 9) of the subject orthopedic element 100 is captured using the imaging technique, wherein the second image 50 defines a second reference frame 50*a*, and wherein the first reference frame 30*a* is offset from the second reference frame 50*a* at an offset angle θ. The first image 30 and the second image 50 are input images from which data (including spatial data 43) can be extracted. It will be appreciated that in other exemplary embodiments, more than two images may be used. In such embodiments, each input image is desirably separated from the other input images by an offset angle θ. Step 4*a* comprises projecting spatial data 43 from the first image 30 of the subject orthopedic element 100 and the spatial data 43 from the second image 50 of the subject orthopedic element 100 to define volume data 75 (FIG. 11) using epipolar geometry.

Step 5*a* comprises using a deep learning network to detect a bone aberration 115 from the volume data 75 of the orthopedic element 100. Step 6*a* comprises using a deep learning network to detect other features (e.g., anatomical landmarks) from the volume data 75 of the subject orthopedic element 100 to define a 3D model of the subject orthopedic element 1100. Step 7*a* comprises applying a surface adjustment algorithm to remove the detected bone aberration 115 from the 3D model of the subject orthopedic element 1100.

In certain exemplary embodiments, the deep learning network that detects the bone aberration 115 from the volume data 75 can be the same deep learning network that detects other features from the volume data 75 of the subject orthopedic element 100. In other exemplary embodiments, the deep learning network that detects the bone aberration 115 from the volume data 75 can be a different from the deep learning network that detects other feature from the volume data 75 of the subject orthopedic element 100.

In certain exemplary embodiments, the first image 30 can depict the subject orthopedic element 100 in a lateral transverse position (i.e., the first image 30 is a lateral view of the orthopedic element 100). In other exemplary embodiments, the second image 50 can depict the orthopedic element 100 in an anterior-posterior ("AP") transverse position (i.e., the second image 50 is an AP view of the orthopedic element 100). In yet other exemplary embodiments, the first image 30 can depict the orthopedic element 100 in an AP transverse position. In still other exemplary embodiments, the second image 50 can depict the orthopedic element 100 in a lateral transverse position. In still yet other exemplary embodiments, neither the first image 30 nor the second image 50 can depict the orthopedic element 100 in an AP transverse position or a lateral transverse position, provided that the first image 30 is offset from the second image 50 by an offset angle 9. The computational machine 1600 can calculate the offset angle θ from input images 30, 50 that include the calibration jig (see 973, FIG. 9). The first image 30 and second image 50 may be referred to collectively as "input images" or individually as an "input image." These input images 30, 50 desirably depict the same subject orthopedic element 100 from different angles. These input images 30, 50 can be taken along a transverse plane of the subject orthopedic element 100.

Certain exemplary methods can further comprise using a style transfer deep learning network such as Cycle-GAN. Methods that use a style transfer deep learning network may start with a radiographic input image (e.g., 30) and use the style transfer neural network to transfer the style of the input image to a DRR type image. Yet further exemplary methods may comprise using a deep learning network to identify features (e.g., anatomical landmarks) of the subject orthopedic element 100 or bone aberration 115 to provide a segmentation mask for each subject orthopedic element 100 or bone aberration 115.

Figure 10:
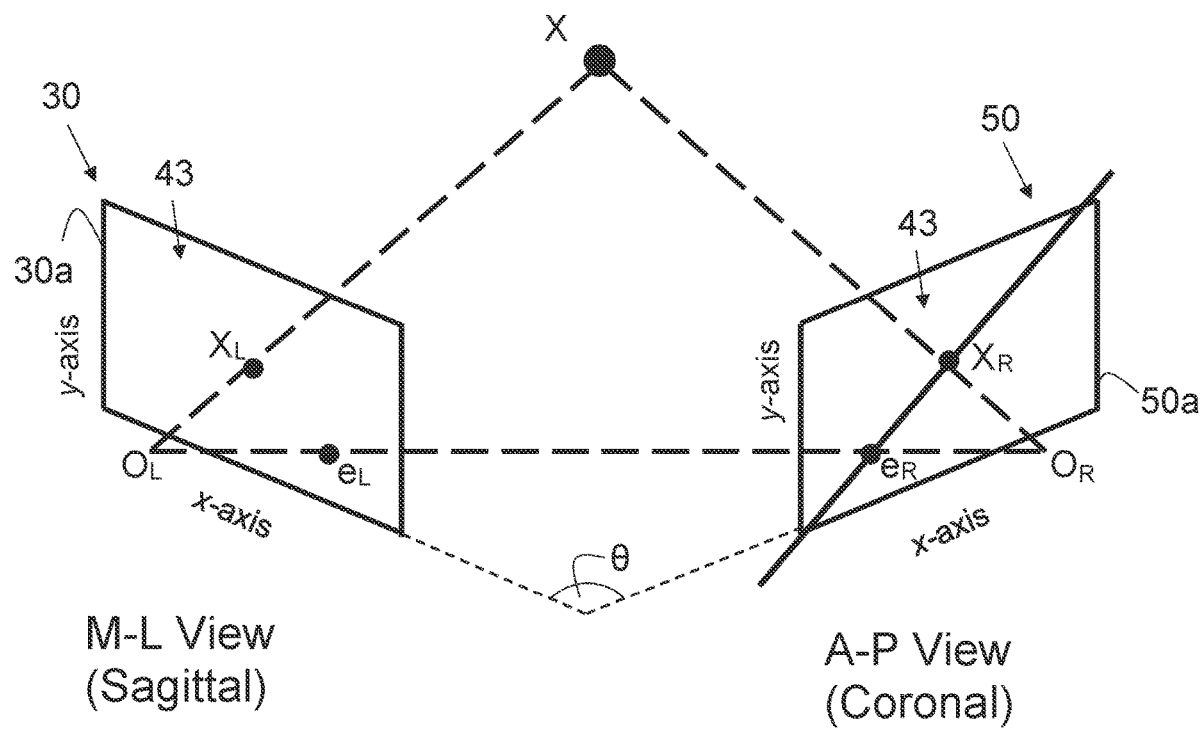
FIG. 10 is a schematic depiction of a pinhole camera model used to convey how principles of epipolar geometry can be used to ascertain the position of a point in 3D space from two 2D images taken from different reference frames from calibrated image detectors.
Figure 11:
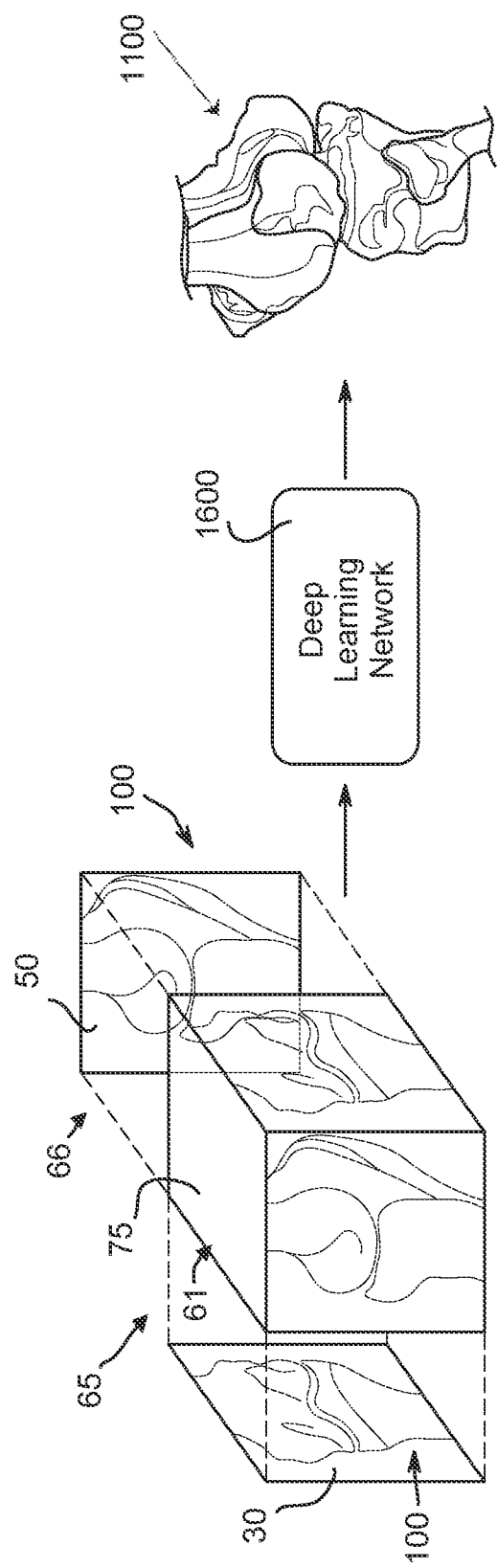
FIG. 11 is a schematic depiction of a system that uses a deep learning network to identify features (e.g., anatomical landmarks) of a subject orthopedic element, including bone aberrations, and to generate a 3D model of the subject orthopedic element.

FIGS. 10 and 11 illustrate how the first input image 30 and the second input image 50 can be combined to create a volume 61 comprising volume data 75. FIG. 10 illustrates basic principles of epipolar geometry than can be used to convert spatial data 43 from the respective input images 30, 50 into volume data 75 (FIG. 11). It will be appreciated that the spatial data 43 is defined by a collection of image points (e.g., $X_L$, $X_R$) mapped to corresponding space coordinates (e.g., x and y coordinates) for a given input image 30, 50.

Figure 18:
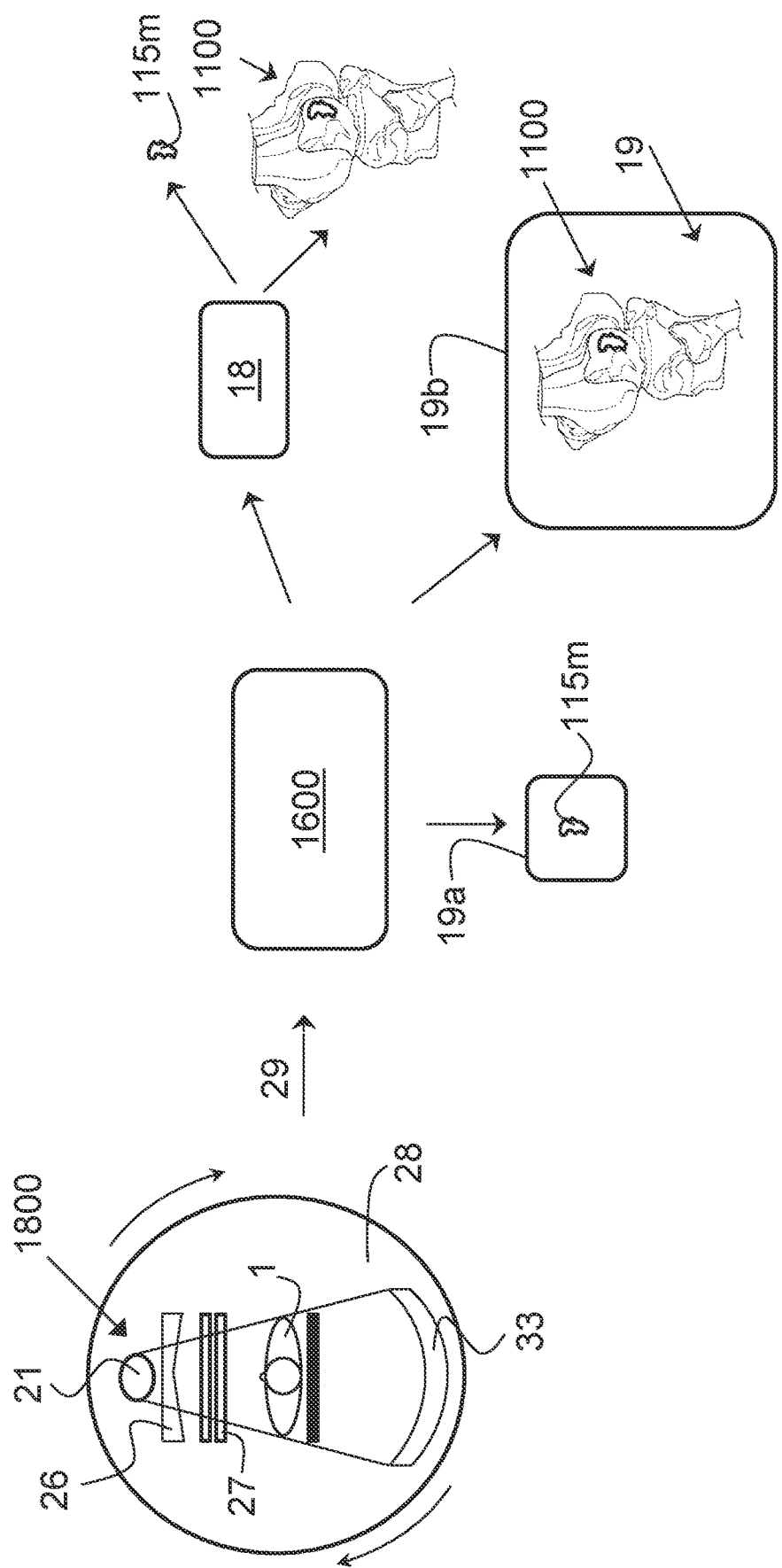
FIG. 18 is a schematic representation of an exemplary system.

FIG. 10 is a simplified schematic representation of a perspective projection described by the pinhole camera model. FIG. 10 conveys basic concepts related to computer stereo vison, but it is by no means the only method by which 3D models can be reconstructed from 2D stereo images. In this simplified model, rays emanate from the optical center (i.e., the point within a lens at which the rays of electromagnetic radiation (e.g., visible light, X-rays, etc.) from the subject object are assumed to cross within the imaging machine's sensor or detector array 33 (FIG. 18). The optical centers are represented by points $O_L$, $O_R$ in FIG. 10. In reality, the image plane (see 30a, 50a) is usually behind the optical center (e.g., $O_L$, $O_R$) and the actual optical center is projected onto the detector array 33 as a point, but virtual image planes (see 30a, 50a) are presented here for illustrating the principles more simply.

The first input image 30 is taken from a first reference frame 30a, while the second input image 50 is taken from a second reference frame 50a that is different from the first reference frame 30a. Each image comprise a matrix of pixel values. The first and second reference frames 30a, 50a are desirably offset from one another by an offset angle θ. The offset angle θ can represent the angle between the x-axis of the first reference frame 30a relative to the x-axis of the second reference frame 50a. Point $e_L$ is the location of the second input image's optical center $O_R$ on the first input image 30. Point $e_R$ is the location of the first input image's optical center $O_L$ on the second input image 50. Points $e_L$ and $e_R$ are known as "epipoles" or epipolar points and lie on line $O_L$-$O_R$. The points X, $O_L$, $O_R$ define an epipolar plane.

Because the actual optical center is the assumed point at which incoming rays of electromagnetic radiation from the subject object cross within the detector lens, in this model, the rays of electromagnetic radiation can actually be imagined to emanate from the optical centers $O_L$, $O_R$ for the purpose of visualizing how the position of a 3D point X in 3D space can be ascertained from two or more input images 30, 50 captured from a detector 33 of known relative position. If each point (e.g., $X_L$) of the first input image 30 corresponds to a line in 3D space, then if a corresponding point (e.g., $X_R$) can be found in the second input image, then these corresponding points (e.g., $X_L$, $X_R$) must be the projection of a common 3D point X. Therefore, the lines generated by the corresponding image points (e.g., $X_L$, $X_R$) must intersect at 3D point X. In general, if the value of X is calculated for every corresponding image points (e.g., $X_L$, $X_R$) in two or more input images 30, 50, a 3D volume 61 comprising volume data 75 can be reproduced from the two or more input images 30, 50. The value of any given 3D point X can be triangulated in a variety of ways. A non-limiting list of example calculation methods include the mid-point method, the direct linear transformation method, the essential matrix method, the line-line intersection method, and the bundle adjustment method.

It will be appreciated that "image points" (e.g., $X_L$, $X_R$) described herein may refer to a point in space, a pixel, a portion of a pixel, or a collection of adjacent pixels. It will also be appreciated that 3D point X as used herein can represent a point in 3D space. In certain exemplary applications, 3D point X may be expressed as a voxel, a portion of a voxel, or a collection of adjacent voxels.

However, before principles of epipolar geometry can be applied, the position of each image detector 33 relative to the other image detector(s) 33 must be determined (or the position of a sole image detector 33 must be determined at the point in time in which the first image 30 was taken and the adjusted position of the sole image detector 33 should be known at the point in time in which the second image 50 was taken). It is also desirable to determine the focal length and the optical center of the imaging machine 1800. To ascertain this practically, the image detector 33 (or image detectors) is/are first calibrated. FIGS. 9A and 9B depict calibration jigs 973A, 973B relative to subject orthopedic elements 100. In these figures, the example orthopedic elements 100 are the distal aspect of the femur 105 and the proximal aspect of the tibia 110 that comprise a knee joint. The proximal fibula 111 is another orthopedic element 100 imaged in FIGS. 9A and 9B. The patella 901 is another orthopedic element 100 shown in FIG. 9B.

FIG. 9A is an anterior-posterior view of the example orthopedic elements 100 (i.e., FIG. 9A represents a first image 30 taken from a first reference frame 30a). A first calibration jig 973A is attached to a first holding assembly 974A. The first holding assembly 974A may comprise a first padded support 971A engaged to a first strap 977A. The first padded support 971A is attached externally to the patient's thigh via the first strap 977A. The first holding assembly 974A supports the first calibration jig 973A oriented desirably parallel to the first reference frame 30a (i.e., orthogonal to the detector 33). Likewise, a second calibration jig 973B that is attached to a second holding assembly 974B may be provided. The second holding assembly 974B may comprise a second padded support 971B engaged to a second strap 977B. The second padded support 971B is attached externally to the patient's calf via the second strap 977B. The second holding assembly 974B supports the second calibration jig 973B desirably parallel to the first reference frame 30a (i.e., orthogonal to the detector 33). The calibration jigs 973A, 973B are desirably positioned sufficiently far away from the subject orthopedic elements 100 such that the calibration jigs 973A, 973B do not overlap any subject orthopedic element 100.

FIG. 9B is a medial-lateral view of the example orthopedic elements 100 (i.e., FIG. 9B represents a second image 50 taken from a second reference frame 50a). In the depicted example, the medial-lateral reference frame 50a is rotated or "offset" 90° from the anterior-posterior first reference frame 30a. The first calibration jig 973A is attached to the first holding assembly 974A. The first holding assembly 974A may comprise a first padded support 971A engaged to a first strap 977A. The first padded support 971A is attached externally to the patient's thigh via the first strap 977A. The first holding assembly 974A supports the first calibration jig 973A desirably parallel to the second reference frame 50a (i.e., orthogonal to the detector 33). Likewise, a second calibration jig 973B that is attached to a second holding assembly 974B may be provided. The second holding assembly 974B may comprise a second padded support 971B engaged to a second strap 977B. The second padded support 971B is attached externally to the patient's calf via the second strap 977B. The second holding assembly 974B supports the second calibration jig 973B desirably parallel to the second reference frame 50a (i.e., orthogonal to the detector 33). The calibration jigs 973A, 973B are desirably positioned sufficiently far away from the subject orthopedic elements 100 such that the calibration jigs 973A, 973B do not overlap any subject orthopedic element 100.

The patient can desirably be posited in the standing position (i.e., the leg is in extension) because the knee joint is stable in this orientation (see FIG. 18). Preferably, the patient's distance relative to the imaging machine should not be altered during the acquisition of the input images 30, 50. The first and second images 30, 50 need not capture the entire leg, rather the image can focus on the joint that will be the subject of the operative area 170.

It will be appreciated that depending upon the subject orthopedic element 100 to be imaged modeled, only a single calibration jig 973 may be used. Likewise, if a particularly long collection of orthopedic elements 100 are to be imaged and modeled, more than two calibration jigs may be used.

Each calibration jig 973A, 973B is desirably of a known size. Each calibration jig 973A, 973B desirably has at least four or more calibration points 978 distributed throughout. The calibration points 978 are distributed in a known pattern in which the distance from one point 978 relative to the others is known. The distance from the calibration jig 973 from an orthopedic element 100 can also be desirably known. For calibration of an X-ray photogrammetry system, the calibration points 978 may desirably be defined by metal structures on the calibration jig 973. Metal typically absorbs most X-ray beams that contact the metal. As such, metal typically appears very brightly relative to material that absorbs less of the X-rays (such as air cavities or adipose tissue). Common example structures that define calibration points include reseau crosses, circles, triangles, pyramids, and spheres.

These calibration points 978 can exist on a 2D surface of the calibration jig 973, or 3D calibration points 978 can be captured as 2D projections from a given image reference frame. In either situation, the 3D coordinate (commonly designated the z coordinate) can be set to equal zero for all calibration points 978 captured in the image. The distance between each calibration point 978 is known. These known distances can be expressed as x, y coordinates on the image sensor/detector 33. To map a point in 3D space to a 2D coordinate pixel on a sensor 33, the dot product of the detector's calibration matrix, the extrinsic matrix and the homologous coordinate vector of the real 3D point can be used. This permits the real world coordinates of a point in 3D space to be mapped relative to calibration jig 973. Stated differently, this generally permits the x, y coordinates of the real point in 3D space to be transformed accurately to the 2D coordinate plane of the image detector's sensor 33 to define spatial data 43 (see FIG. 10).

The above calibration method is provided as an example. It will be appreciated that all methods suitable for calibrating an X-ray photogrammetry system are considered to be within the scope of this disclosure. A non-limiting list of other X-ray photogrammetry system calibration methods include the use of a reseau plate, the Zhang method, the bundle adjustment method, direct linear transformation methods, maximum likelihood estimation, a k-nearest neighbor regression approach ("kNN"), other deep learning methods, or combinations thereof.

FIG. 11 illustrates how the calibrated input images 30, 50, when oriented along the known offset angle θ, can be back projected into a 3D volume 61 comprising two channels 65, 66. The first channel 65 contains all the image points (e.g., $X_L$ etc.) of the first input image 30 and the second channel 66 contains all the image points (e.g., $X_R$ etc.) of the second input image 50. That is, each image point (e.g., pixel) is replicated over its associated back-projected 3D ray. Next, epipolar geometry can be used to generate a volume 61 of the imaged operative area 170 comprising volume data 75 from these back projected 2D input images 30, 50.

Referring to FIG. 11, the first image 30 and the second image 50 desirably have known image dimensions. The dimensions may be pixels. For example, the first image 30 may have dimensions of 128×128 pixels. The second image 50 may have dimensions of 128×128 pixels. The dimensions of the input images 30, 50 used in a particular computation desirably have consistent dimensions. Consistent dimensions may be desirable for later defining a cubic working area of regular volume 61 (e.g., a 128×128×128 cube). As seen in FIG. 10, the offset angle θ is desirably 90°. However, other offset angles θ may be used in other exemplary embodiments.

In the depicted example, each of the 128×128 pixel input images 30, 50 are replicated 128 times over the length of the adjacent input image to create a volume 61 having dimensions of 128×128×128 pixels. That is, the first image 30 is copied and stacked behind itself at one copy per pixel for 128 pixels while the second image 50 is copied and stacked behind itself for 128 pixels such that stacked images overlap to thereby create the volume 61. In this manner, the volume 61 can be said to comprise two channels 65, 66, wherein the first channel 65 comprises the first image 30 replicated n times over the length of the second image 50 (i.e., the x-axis of the second image 50) and the second channel 66 comprises the second image 50 replicated m times over the length of the first image 30 (i.e., the x-axis of the first image 30), wherein "n" and "m" are the length of the indicated image as expressed as the number of pixels (or other dimensions on other exemplary embodiments) that comprise the length of the indicated image. If the offset angle θ is known, each transverse slice (also known as an "axial slice" by some radiologists) of the volume 61 creates an epipolar plane comprising voxels that are back-projected from the pixels that comprise the two epipolar lines. In this manner, projecting spatial data 43 from the first image 30 of the subject orthopedic element 100 and the spatial data 43 from the second image 50 of the subject orthopedic element 100 to defines volume data 75. Using this volume data 75, the 3D representation can be reconstructed using epipolar geometric principles as discussed above; the 3D representation is consistent geometrically with the information in the input images 30, 50.

In exemplary systems and methods for calculating an area of bone aberration 115 using a deep learning network, wherein the deep learning network is a CNN, a detailed example of how the CNN can be structured and trained is provided. All architecture of CNNs are considered to be within the scope of this disclosure. Common CNN architectures include by way of example, LeNet, GoogLeNet, AlexNet, ZFNet, ResNet, and VGGNet.

Figure 17:
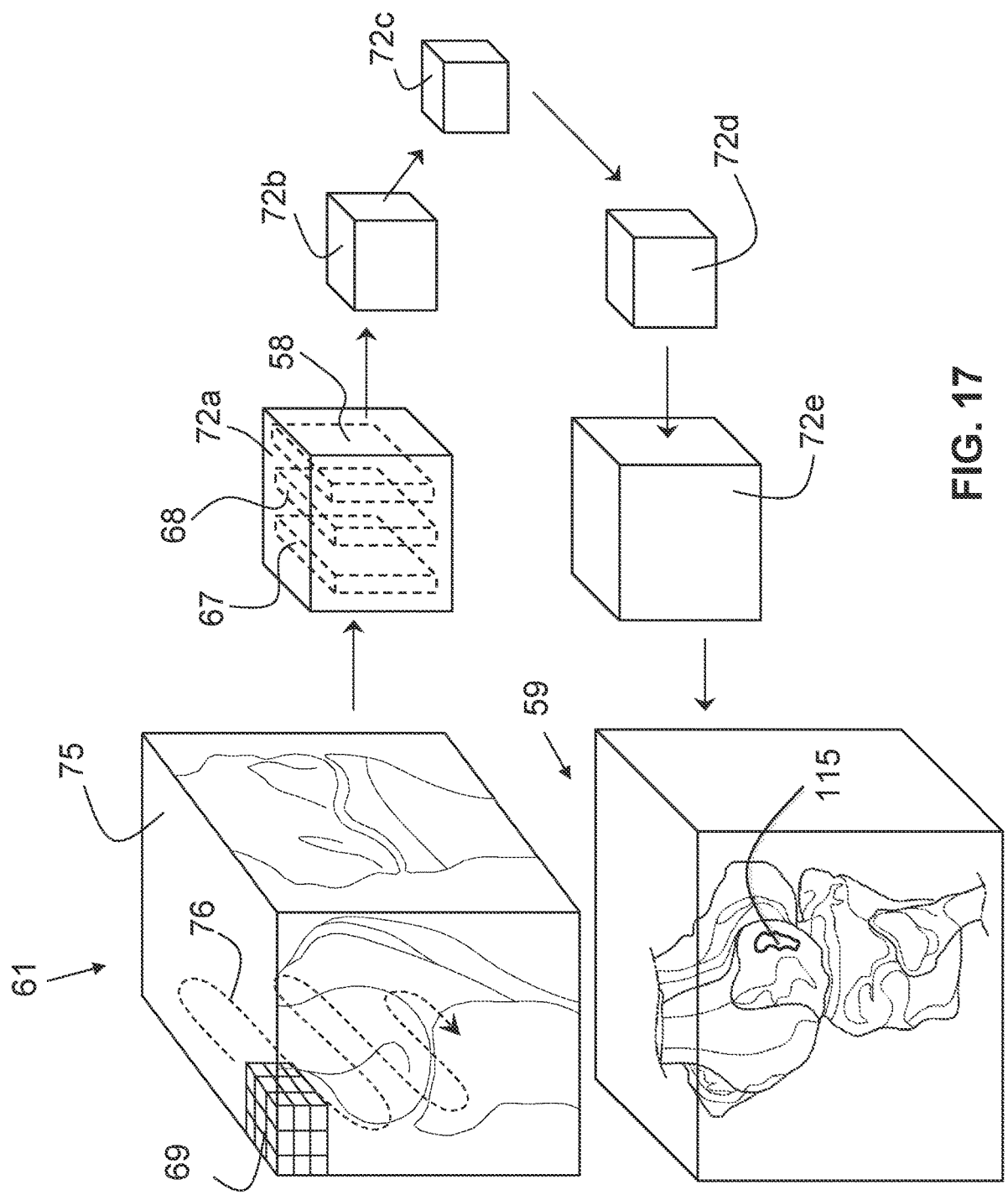
FIG. 17 is a schematic representation depicting how a CNN type deep learning network can be used to identify features (e.g., anatomical landmarks), including bone aberrations of a subject orthopedic element.

FIG. 17 is a schematic representation of a CNN that illustrates how the CNN can be used to identify areas of bone aberrations 115. Without being bound by theory, it is contemplated that a CNN may be desirable for reducing the size of the volume data 75 without losing features that are necessary to identify the desired orthopedic element or the desired areas of bone aberration 115. The volume data 75 of the multiple back projected input images 30, 50 is a multi-dimensional array that can be known as an "input tensor." This input tensor comprises the input data (which is the volume data 75 in this example) for the first convolution. A filter (also known as a kernel 69) is shown disposed in the volume data 75. The kernel 69 is a tensor (i.e., a multi-dimensional array) that defines a filter or function (this filter or function is sometimes known as the "weight" given to the kernel). In the depicted embodiment, the kernel tensor 69 is three dimensional. The filter or function that comprises the kernel 69 can be programed manually or learned through the CNN, RNN, or other deep learning network. In the depicted embodiment, the kernel 69 is a 3×3×3 tensor although all tensor sizes and dimensions are considered to be within the scope of this disclosure, provided that the kernel tensor size is less than the size of the input tensor.

Each cell or voxel of the kernel 69 has a numerical value. These values define the filter or function of the kernel 69. A convolution or cross-correlation operation is performed between the two tensors. In FIG. 17, the convolution is represented by the path 76. The path 76 that the kernel 69 follows is a visualization of a mathematical operation. Following this path 76, the kernel 69 eventually and sequentially traverses the entire volume 61 of the input tensor (e.g., the volume data 75). The goal of this operation is to extract features from the input tensor.

Convolution layers 72 typically comprise one or more of the following operations: a convolution stage 67, a detector stage 68, and a pooling stage 58. Although these respective operations are represented visually in the first convolution layer 72a in FIG. 17, it will be appreciated that the subsequent convolution layers 72b, 72c, etc. may also comprise one or more or all of the convolution stage 67, detector stage 68, and pooling layer 58 operations or combinations or permutations thereof. Furthermore, although FIG. 17, depicts five convolution layers 72a, 72b, 72c, 72d, 72e of various resolutions, it will be appreciated that more or less convolution layers may be used in other exemplary embodiments.

In the convolution stage 67, the kernel 69 is sequentially multiplied by multiple patches of pixels in the input data (i.e., the volume data 75 in the depicted example). The patch of pixels extracted from the data is known as the receptive field. The multiplication of the kernel 69 and the receptive field comprises an element-wise multiplication between each pixel of the receptive field and the kernel 69. After multiplication, the results are summed to form one element of a convolution output. This kernel 69 then shifts to the adjacent receptive field and the element-wise multiplication operation and summation continue until all the pixels of the input tensor have been subjected to the operation.

Until this point, the input data (e.g., the volume data 75) of the input tensor has been linear. To introduce non-linearity to this data, a nonlinear activation function is then employed. Use of such a non-linear function marks the beginning of the detector stage 68. A common non-linear activation function is the Rectified Linear Unit function ("ReLU"), which is given by the function:

$$ReLU(x) = \left\{ \begin{array}{l} 0, \text{ if } x < 0 \\ x, \text{ if } x \geq 0 \end{array} \right\}$$

When used with bias, the non-linear activation function serves as a threshold for detecting the presence of the feature extracted by the kernel 69. For example, applying a convolution or a cross-correlation operation between the input tensor and the kernel 69, wherein the kernel 69 comprises a low level edge filter in the convolution stage 67 produces a convolution output tensor. Then, applying a non-linear activation function with a bias to the convolution output tensor will return a feature map output tensor. The bias is sequentially added to each cell of the convolution output tensor. For a given cell, if the sum is greater than or equal to 0 (assuming ReLU is used in this example), then the sum will be returned in the corresponding cell of the feature map output tensor. Likewise, if the sum is less than 0 for a given cell, then the corresponding cell of the feature map output tensor will be set to 0. Therefore, applying non-linear activations functions to the convolution output behaves like a threshold for determining whether and how closely the convolution output matches the filter of the kernel 69. In this manner, the non-linear activation function detects the presence of the desired features from the input data (e.g., the volume data 75 in this example).

All non-linear activation functions are considered to be within the scope of this disclosure. Other examples include the Sigmoid, TanH, Leaky ReLU, parametric ReLU, Softmax, and Switch activation functions.

However, a shortcoming of this approach is that the feature map output of this first convolutional layer 72a records the precise position of the desired feature (in the above example, an edge). As such, small movements of the feature in the input data will result in a different feature map. To address this problem and to reduce computational power, down sampling is used to lower the resolution of the input data while still preserving the significant structural elements. Down sampling can be achieved by changing the stride of the convolution along the input tensor. Down sampling is also achieved by using a pooling layer 58.

Valid padding may be applied to reduce the dimensions of the convolved tensor (see 72b) compared to the input tensor (see 72a). A pooling layer 58 is desirably applied to reduce the spatial size of the convolved data, which decreases the computational power required to process the data. Common pooling techniques, including max pooling and average pooling may be used. Max pooling returns the maximum value of the portion of the input tensor covered by the kernel 69, whereas average pooling returns the average of all the values of the portion of the input tensor covered by the kernel 69. Max pooling can be used to reduce image noise.

In certain exemplary embodiments, a fully connected layer can be added after the final convolution layer 72e to learn the non-linear combinations of the high level features (such as the profile of an imaged proximal tibia 110 or a bone aberration 115) represented by the output of the convolutional layers.

The top half of FIG. 17 represents compression of the input volume data 75, whereas the bottom half represents decompression until the original size of the input volume data 75 is reached. The output feature map of each convolution layer 72a, 72b, 72c, etc. is used as the input for the following convolution layer 72b, 72c, etc. to enable progressively more complex feature extraction. For example, the first kernel 69 may detect edges, a kernel in the first convolution layer 72b may detect a collection of edges in a desired orientation, a kernel in a third convolution layer 72c may detect a longer collection of edges in a desired orientation, etc. This process may continue until the entire profile of the medial distal femoral condyle is detected by a downstream convolution layer 72.

The bottom half of FIG. 17 up-samples (i.e., expands the spatial support of the lower resolution feature maps. A de-convolution operation is performed in order to increase the size of the input for the next downstream convolutional layer (see 72c, 72d, 72e). For the final convolution layer 72e, a convolution can be employed with a 1×1×1 kernel 69 to produce a multi-channel output volume 59 that is the same size as the input volume 61. Each channel of the multi-channel output volume 59 can represent a desired extracted high level feature. This can be followed by a Softmax activation function to detect the desired orthopedic elements 100. For example, the depicted embodiment may comprise six output channels numbered 0, 1, 2, 3, 4, 5 wherein channel 0 represents identified background volume, channel 1 represents the identified distal femur 105, channel 2 represents the identified proximal tibia 110, channel 3 represents the identified proximal fibula 111, channel 4 represents the identified patella 901, and channel 5 represents the identified bone aberration 115.

In exemplary embodiments, select output channels comprising output volume data 59 of the desired orthopedic element 100 or bone aberration 115b can be used to create a 3D model of the subject orthopedic element 1100 or a 3D model of the bone aberration 115m.

Although the above example described the use of a three dimensional tensor kernel 69 to convolve the input volume data 75, it will be appreciated that the general model described above can be used with a of 2D spatial data 43 from the first calibrated input image 30 and the second calibrated input image 50 respectively. In other exemplary embodiments, a machine learning algorithm (i.e., a deep learning network (such as for example, a CNN)) can be used after calibration of the imaging machine but before 2D to 3D reconstruction. That is, the CNN can be used to detect features (e.g., anatomical landmarks) of a subject orthopedic element 100 from the first reference frame 30a and the second reference frame 50s of the respective 2D input images 30, 50. In exemplary embodiments, CNN may be used to identify high level orthopedic elements (e.g., the distal femur 105 and any bone aberrations 115) from the 2D input images 30, 50. The CNN may then optionally apply a mask or an outline to the detected orthopedic element 100 or bone aberration 115. It is contemplated that is the imaging machine 1800 is calibrated and if the CNN identified multiple corresponding image points (e.g., $X_L$, $X_R$) of features between the two input images 30, 50, then the transformation matrices between the reference frames 30a, 50a of a subject orthopedic element 100 can be used to align the multiple corresponding image points in 3D space.

In certain exemplary embodiments that comprise using a deep learning network to add a mask or an outline to the detected 2D orthopedic element 100 or bone aberration 115 from the respective input images 30, 50, only the 2D masks or outlines of the identified orthopedic element 100 or bone aberration 115 can be sequentially back-projected in the manner described with reference to FIGS. 10 and 11 supra to define a volume 61 of the identified orthopedic element 100 or bone aberration 115. In this exemplary manner, a 3D model of the subject orthopedic element 1100 or a 3D model of the bone aberration 115m may be created.

In embodiments wherein the first image 30 and the second image 50 are radiographic X-ray images, training a CNN can present several challenges. By way of comparison, CT scans typically produce a series of images of the desired volume. Each CT image that comprises a typical CT scan can be imagined as a segment of the imaged volume. From these segments, a 3D model can be created relatively easily by adding the area of the desired element as the element is depicted in each successive CT image. The modeled element can then be compared with the data in the CT scan to ensure accuracy.

By contrast, radiographic imaging systems typically do not generate sequential images that capture different segments of the imaged volume; rather, all of the information of the image is flattened on the 2D plane. Additionally, because a single radiographic image 30 inherently lacks 3D data, it is difficult to check the model generated by the epipolar geometry reconstruction technique described above with the actual geometry of the target orthopedic element 100. To address this issue, the CNN can be trained with CT images, such as digitally reconstructed radiograph ("DRRs") images. By training the neural network in this way, the neural network can develop its own weights (e.g., filters) for the kernels 69 to identify a desired orthopedic element 100 or a bone aberration 115b. Because X-ray radiographs have a different appearance than DRRs, image-to-image translation can be performed to render the input X-ray images to have a DRR-style appearance. An example image-to-image translation method is the Cycle-GAN image translation technique. In embodiments in which image-to-image style transfer methods are used, the style transfer method is desirably used prior to imputing the data into a deep learning network for feature detection.

The above examples are provided for illustrative purposes and are in no way intended to limit the scope of this disclosure. All methods for generating a 3D model of the subject orthopedic element 1100 or a 3D model of the bone aberration 115m from 2D radiographic images of the same subject orthopedic element 100 taken from at least two transverse positions (e.g., 30s, 50a) are considered to be within the scope of this disclosure.

Figure 12:
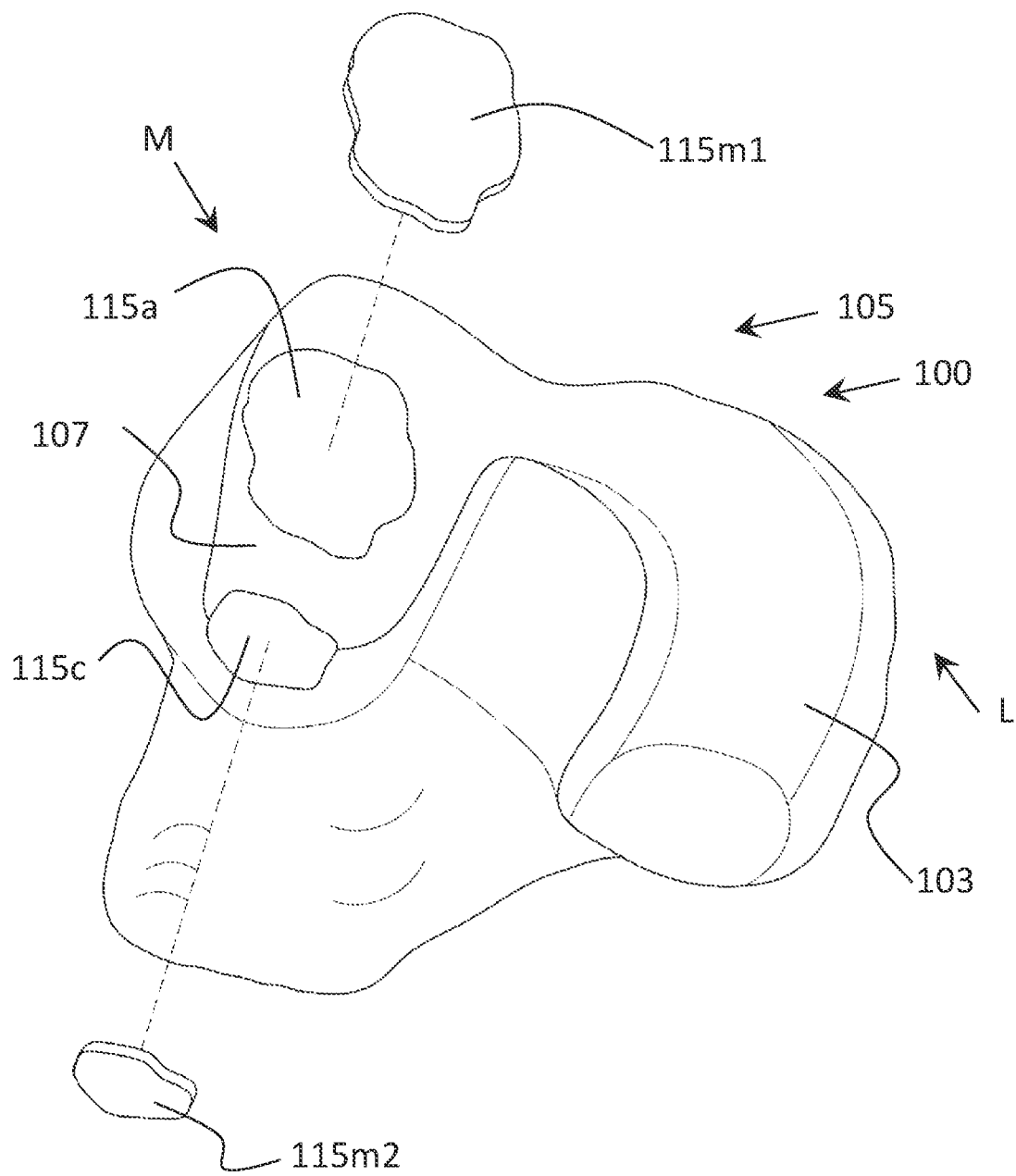
FIG. 12 is a schematic perspective depiction of the distal aspect of a femur and two 3D reconstructed models of the inverse volume of the identified negative bone aberration.

FIG. 12 is a perspective view that depicts a distal femur 105 and 3D models of bone aberrations 115m1, 115m2. It will be appreciated that the 3D models of the bone aberrations 115m1, 115m2 can be produced in accordance with any method or system of this disclosure. In the depicted embodiment, the distal femur 105 had two negative bone aberrations 115a, 115c (i.e., areas of bone loss) on the medial condyle 107. A method in accordance with this disclosure can be used to identify the bone aberrations 115a, 115c, as described herein. The output channel comprising the bone aberration volume data 59 can be used to produce a 3D model of the bone aberration 115m1. In the depicted example, the respective 3D models of the bone aberrations 115m1, 115m2 comprise the inverse volume of actual bone aberrations 115a, 115c. To delineate the boundary of the volume that comprises the 3D models of the bone aberrations 115m1, 115m2, the deep learning network can be trained to detect the edges of the actual negative bone aberrations 115a, 115c and the curvature of the surface of the adjacent orthopedic element 100 in which the negative bone aberration 115a, 115c resides. In the depicted example, the surface of the adjacent orthopedic element is the medial condylar surface. A surface adjustment algorithm, such as for example, a curve-fitting algorithm, can then be applied to estimate the curvature of the missing surface to thereby correct the negative bone aberration 115. In embodiments, the estimated curvature can then be added to the identified surface area of the negative bone aberration (e.g., 115a). The space between the identified surface area of the negative bone aberration and the estimated curvature defines the modeled volume of the negative bone aberration 115a. The data comprising this modeled volume can be used to produce a 3D model of the aberration 115m1 that has an inverse modeled volume to the actual volume of the negative bone aberration 1159.

It will be appreciated that in embodiments in which the bone aberration 115 is a positive bone aberration 115 (e.g., an osteophyte), a deep learning network can be trained to detect the edges of the actual positive bone aberration 115 and the curvature of the surface of the adjacent orthopedic element 100 on which the positive bone aberration 115 resides. If the surface of the adjacent orthopedic element 100 is curved, a curve-fitting algorithm can be used to estimate the curvature of the surface without the positive bone aberration 115 to thereby correct the positive bone aberration 115.

In certain exemplary embodiments, a 3D model of the bone aberration 115m1 can be produced as a physical 3D bone aberration model. If used intraoperatively, the physical 3D model of the bone aberration 115m1 may be created at 1:1 scale. In such exemplary embodiments, the physical 3D model of the bone aberration 115m1 may be made from a medical-grade polyamide (informally known as nylon). The material of the physical 3D model of the bone aberration 115m1 should be sterilizable and can desirably have properties suitable for an autoclave. Autoclaves are generally small and compact, which makes them especially useful for sterilizing the physical 3D model of the bone aberration 115m1 at or near the surgical center.

Other examples of suitable materials for the 3D model of the bone aberration 115m1 include a medical grade polyethylene (e.g., ultra-high molecular weight polyethylene ("UHMWPE"), a polyether ether ketone ("PEEK"), or other biocompatible, clinically proven materials, including but not limited to, cobalt chrome molybdenum alloys, titanium alloys, and ceramic materials, including but not limited to zirconia toughened alumina ("ZTA") ceramics. In situations in which the bone aberration is an area of bone loss, an advantage of a 1:1 physical 3D model of the bone aberration 115m1 is that the physical 3D model of the bone aberration 115m1 has a complementary surface of the exposed surface 116 of the actual bone aberration (see 115b, FIG. 2, 4). Provided that the physical 3D bone aberration model 115m1 is properly sterilized, the physical 3D bone aberration model 115m1 can be placed adjacent to the complementary surface 116 of the actual bone aberration 115b intraoperatively. In this manner, the uncertainty described above with reference to FIG. 2 supra is obviated.

In an exemplary embodiment, the physical 3D model of the bone aberration 115m2 can be selectively attached to one or both posterior pads 693a, 693b of the alignment guide 600. It is contemplated that by providing a physical sterilized model of the missing bone, the uncertainty described with reference to FIG. 5 infra is eliminated.

Figure 3:
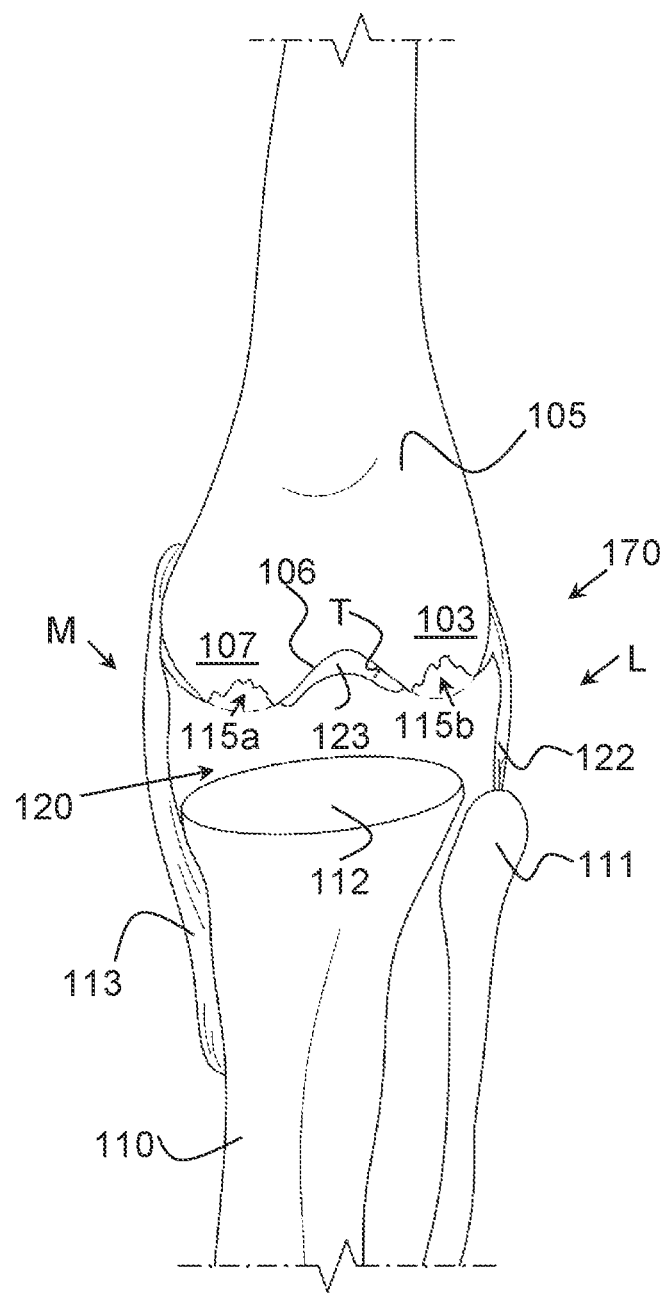
FIG. 3 is an anterior view of a simplified left knee joint visually representing the application of a surface adjustment algorithm to calculate an external missing bone surface that corrects the negative bone aberration.

FIG. 3 is an anterior view of a simplified left knee joint visually representing the step of using a deep learning network to detect a bone aberration 115a, 115b on or in the volume data 75 of the orthopedic element 100. The deep learning network can detect other landmarks from the volume data 75 of the subject orthopedic element 100 to define a 3D model of the subject orthopedic element 1100. A surface adjustment algorithm is then applied to remove the bone aberration 115a, 115b from the 3D model of the subject orthopedic element 1100. In the depicted embodiment, the bone aberration 115a, 115b is removed by calculating an external missing bone surface 117a, 117b that matches the outer surface of the bone aberration 115a, 115b (in this case, the outer surface area of bone loss). A computer platform executing the exemplary method can run software that is trained via artificial intelligence to identify features (i.e., landmarks) on the worn condyles that would be indicative of bone loss on the 3D model. In other exemplary embodiments, a person can manually identify the borders of bone loss via a computer interface to identify the area of the bone aberration 115a, 115b. Once identified, a surface adjustment algorithm may be applied to calculate an external missing bone surface 117a, 117b that fits the outer surface area of the bone aberration 115a, 115b in situations in which the bone aberration constitutes bone loss.

In other exemplary embodiments, the step of using the deep learning network to detect a bone aberration 115a, 115b on or in the volume data 75 of the orthopedic element 100 further comprises generating a 3D model of the bone aberration 115m. If the 3D bone aberration model 115m is a computer model, the 3D bone aberration model 115m may optionally be projected on a display 19, such as a screen. In certain exemplary embodiments, the 3D bone aberration computer model 115m may be projected within the surgeon's field of view to overlay the actual bone aberration 115 in an image of the operative area 170. In still other exemplary embodiments, the 3D bone aberration computer model 115m may be projected within the surgeon's field of view to overlay the actual bone aberration 115 in the patient, such as in the exposed operative area 170. Such a display 19 may be accomplished through an augmented reality device, preferably a head-mounted augmented reality device.

In yet other exemplary embodiments, a physical 3D bone aberration model 115m may be created through a manufacturing technique (see FIG. 18). Said manufacturing technique may comprise a reductive manufacturing method such as through use of a computer numerical control ("CNC") machine or a milling machine. In other exemplary embodiments the manufacturing technique may comprise an additive manufacturing technique such as a 3D printing technique. If the manufacturing technique is an additive manufacturing technique, the physical 3D bone aberration model 115m may be manufactured at the preoperative center, offsite, or on or proximal to the operative premise.

Figure 4:
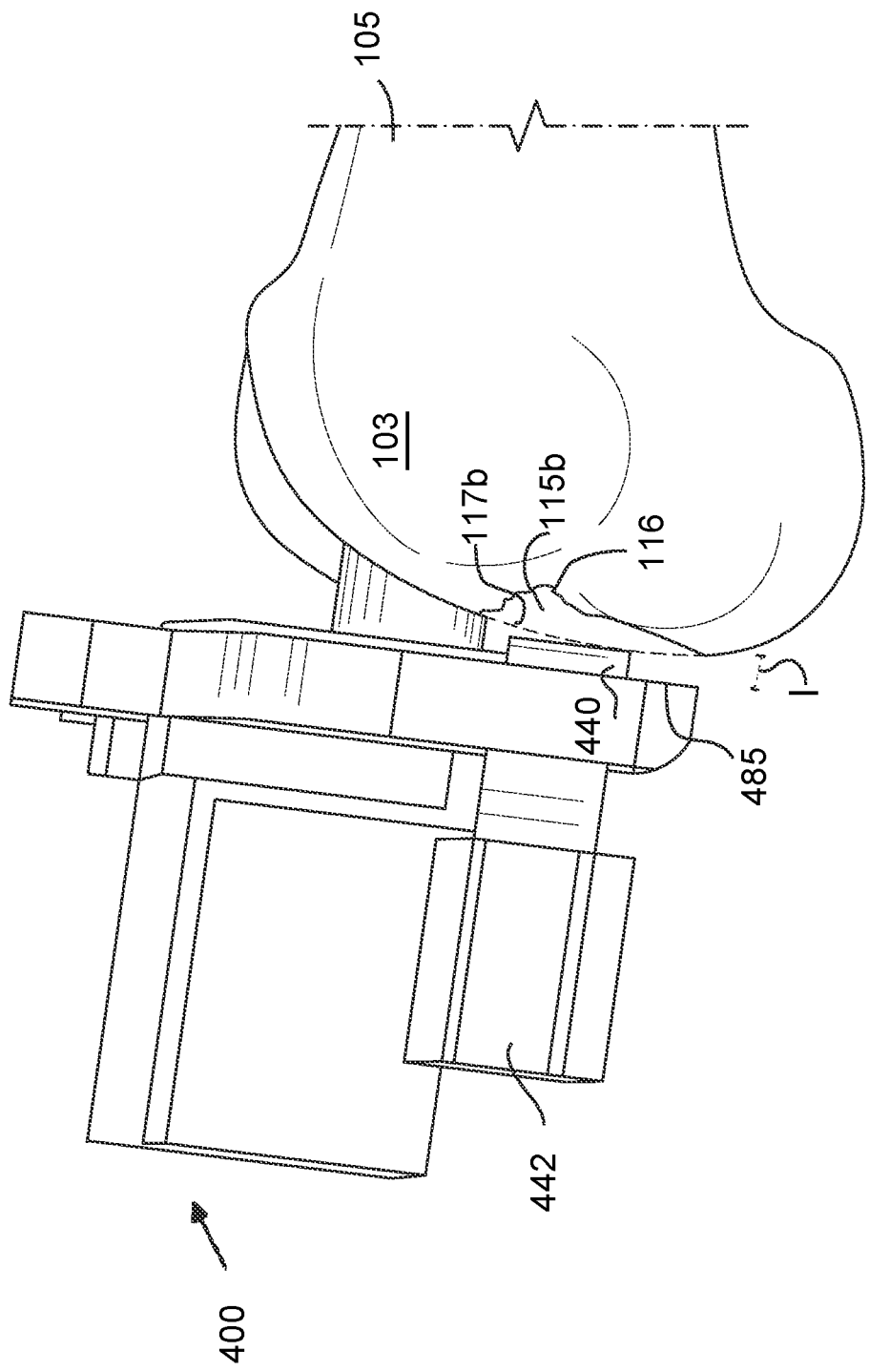
FIG. 4 is a side view of a femoral resection guide positioning instrument having an adjustment pad extending to a calculated external missing bone surface on a lateral femoral condyle.

FIG. 4 is a side view of a pivoting femoral resection guide locator 400 having an adjustment pad 440 with an adjustment knob 442 extending to a calculated external missing bone surface 117b a lateral condyle 103. As can be seen, with the depth of cartilage wear properly ascertained, the adjustment pad 440 can be thought of as extending to the pre-diseased surface of the bone. In practice however, the surgeon may instead choose to add the depth of bone loss to the ascertained depth of cartilage loss, set the length l of the adjustment pad 440 to reflect the combined sum of the maximum bone depth loss and the depth of cartilage loss, and then place the adjustment pad 440 on the remaining exposed bone 116 of the lateral condyle. In this manner, the distal reference surface 485 is now disposed at the articular surface of the pre-diseased joint with precision.

In other exemplary embodiments, a 1:1 physical 3D bone aberration model 115*m* can be affixed to the distal end of the adjustment knob 440 such that a complementary surface of the 1:1 physical 3D bone aberration model 115*m* mates with the surface 116 of the bone aberration 115*b* when the adjustment knob 440 is disposed adjacent to the exposed bone aberration 115*b* (see FIG. 17). In yet other exemplary embodiments in which one of the subject orthopedic elements 100 is the articular cartilage 123 of the distal femur 105, the physical 3D bone aberration model 115*m*1 can comprise the volume of the bone loss as described above plus the modeled surface of the missing cartilage. A surface adjustment algorithm can be used to define the surface of the missing cartilage relative to the surface of the surrounding cartilage.

Figure 5:
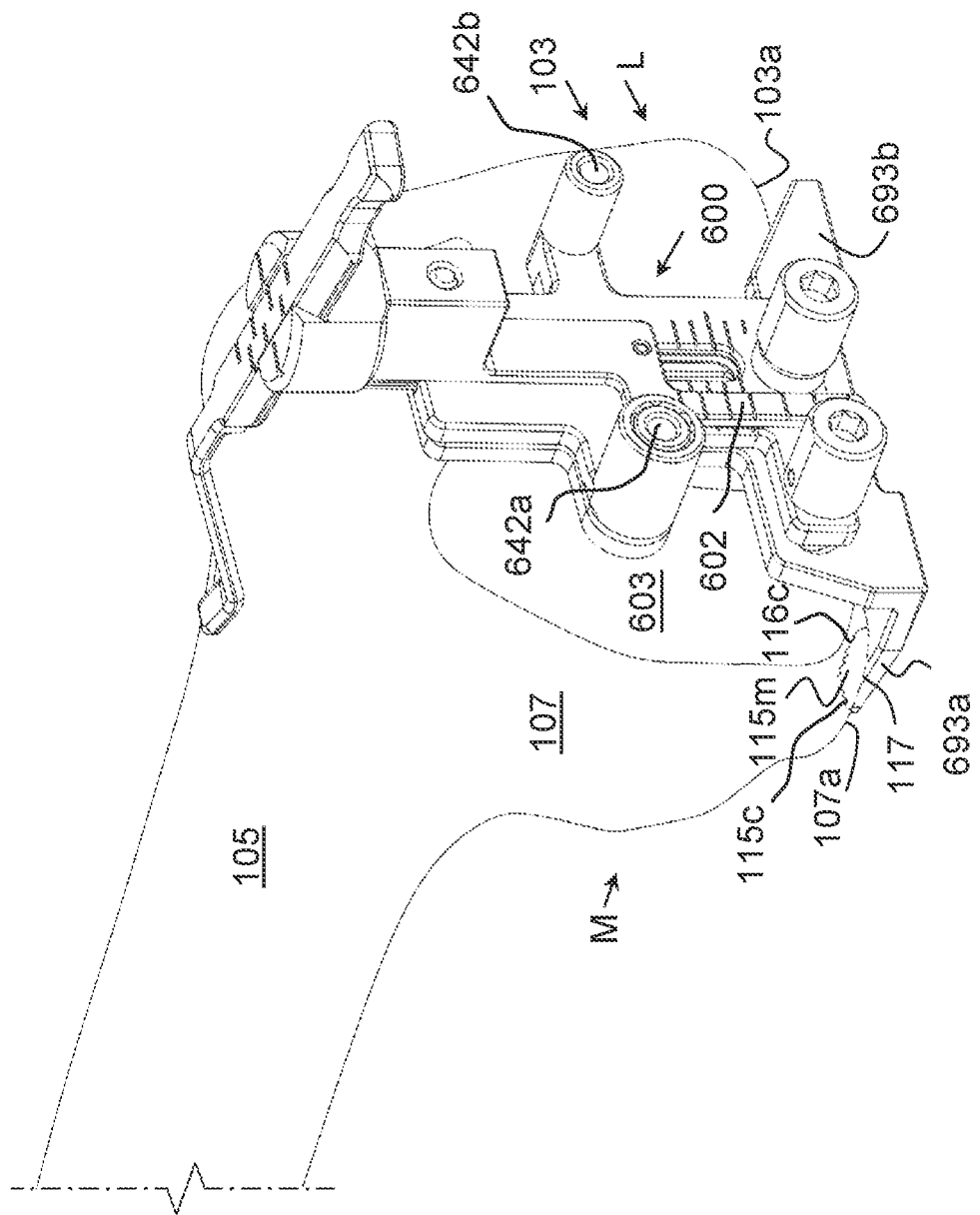
FIG. 5 is a perspective view of a simplified distal femur oriented in flexion. A posterior condyle resection guide positioning instrument is disposed on the posterior portion of the femoral condyles.

FIG. 5 is a perspective view of a simplified distal end of the femur 105 depicted after the distal resection has been made with the resection guide 424. An alignment guide 600 comprising posterior pads 693*a*, 693*b* is disposed under the posterior portion 103*a*, 107*a* of the femoral condyles 103, 107. For simplicity, the posterior portion of the femoral condyles will be referred to as "posterior condyles" 103*a*, 107*a*. The alignment guide 600 can be a combined sizing and alignment guide as depicted herein, or just an alignment guide 600. The alignment guide 600 can comprise a body 602. The posterior pads 693*a*, 693*b* extend from an inferior portion of the body 602 and drill bores 642*a*, 642*b* extend through the body 602 above the posterior pads 693*a*, 693*b*. In the depicted embodiment, a pivot drill bore 642*a* extends through the body 602 of the alignment guide 600 and a radial drill bore 642*b* is disposed radially distal from the pivot drill bore 642*a*. The radial drill bore 642*b* also extends through the body 602 of the alignment guide 600. In practice, the surgeon places the posterior pads 693*a*, 693*b* under the respective posterior condyles 103*a*, 107*a* such that the body 602 is disposed adjacent to the resected surface 603 of the distal femur 105. The surgeon measures the thickness of the remaining articular cartilage on the posterior condyles 103*a*, 107*a* and set the length of the posterior pads 693*a*, 693*b* to reflect the amount of cartilage wear (similar to the way described supra with reference to FIG. 2). Adjustment of the position of the posterior pads 693*a*, 693*b* relative to the body 602 causes the radial drill bore 642*b* to pivot around the pivot drill bore 642*a*. Once the surgeon is satisfied with the angle, the surgeon can lock the angle of the pivoting section of the alignment guide 600 in place.

The surgeon can then drill into the resected surface 603 via the drill bores 642*a*, 642*b* and then insert pins into the respective drill bores 642*a*, 642*b*. The surgeon may then remove the alignment guide 600 and leave the pins. The angle of these pins defines the angle at which further resection guide (commonly known as a "four-in-one cutting block") can be placed next to the resected surface. The four-in-one cutting block has additional resection slots that allow the surgeon to make the anterior, posterior, and chamfer resections using a single "cutting block." These additional resections create a profile on the distal femur 105 upon which trial implants (and eventually the actual endoprosthetic implant) can be placed.

A negative bone aberration (e.g., bone loss) 115*c* can be less common on the posterior portions 103*a*, 107*a* of the femoral condyles 103, 107 but such bone loss is still possible, especially in advanced degenerative diseases. Negative bone aberrations 115*c* of the posterior condyles 103*a*, 107*a* presents similar problems in accurately replicating the natural articular surface of the pre-diseased joint, particularly in kinematic alignment.

For example, if the medial posterior condyle 107*a* has a negative bone aberration 115 as shown in FIG. 5, it was previously impossible to know with certainty how to adjust the depicted alignment guide to account for the amount of bone wear present. Over-adjusting the medial posterior pad 693*a* would change the position of where the respective drill bores 642*a*, 642*b* were located relative to the resected surface 603 and could change the pivot angle of the respective drill bores 642*a*, 642*b*. As a result, the pins could be misplaced. By extension, the position of the four-in-one cutting block would also be displaced by virtue of sliding over misplaced pins. Misplaced anterior, posterior, and chamfer resections could result in imprecisely seating the femoral component of the endoprosthetic implant.

To address this problem, surgeons can measure the amount of articular cartilage wear on the posterior condyles 103*a*, 107*a* in the manners described above, or using other known methods. In other exemplary embodiments, a 1:1 physical 3D bone aberration model 115*m* can be affixed to the end of the posterior pads 693*a*, 693*b* such that a complementary surface (also known as a "mating surface") of the 1:1 physical 3D bone aberration model 115*m* mates with the surface 116*c* of the bone aberration 115*c* when the posterior pad 693*a* is disposed adjacent to the exposed bone aberration 115*c*.

In other exemplary embodiments, the mating surface of the physical 3D bone aberration model can comprise one or more projections (e.g., spike, pins, or other protections). These projections can be hammered or otherwise forcibly inserted through the worn surface 116*c* of the bone aberration 115*c*, to thereby secure the physical model of the bone aberration 115*m* into the negative bone aberration 115*c* to thereby eliminate the negative bone aberration 115*c*. Using an alignment guide 600 with the physical 3D bone aberration model in this manner can ensure more accurate referencing. Furthermore, some four-in-one cutting blocks have markings that are designed to reference the surface of the posterior condyles 107*a*, 103*a*. Using a physical 3D bone aberration model in this manner effectively re-creates the pre-diseased surface of the posterior condyles 107*a*, 103*a* can serve as a visual indicator the four-in-one cutting block (or other instruments as the case may be) are properly aligned with the referenced indicator.

In yet other exemplary embodiments in which one of the subject orthopedic elements 100 is the articular cartilage 123 of the distal femur 105, the physical 3D bone aberration model 115*m*2 can comprise the volume of the bone loss as described above plus the modeled surface of the missing cartilage. A surface adjustment algorithm can be used to define the surface of the missing cartilage relative to the surface of the surrounding cartilage. In this manner, the articular surface of the condyle can be accurately recreated, thereby substantially increasing the precision of the articular surface referencing.

In other exemplary embodiments, a shim, having a height that equals the maximum depth of the negative bone aberration, the depth of the missing articular cartilage, or the combined maximum depth of the negative bone aberration and the depth of the missing articular cartilage can be added to one or more of the posterior pads 693*a*, 693*b* to offset the amount of wear and substantially recreate the position of the pre-diseased articular surface.

A computer platform, having hardware such as one or more central processing units ("CPU"), a random access memory ("RAM"), and input/output ("I/O") interface(s) can receive at least two 2D radiographic images taken at different orientations along a transverse plane. The orientations are preferably orthogonal to each other. The computer platform can then run a machine learning software application that identifies an area of bone loss 115a, 115b, 115c and that applies a surface adjustment algorithm to calculate an external missing bone surface 117a, 117b, 117c that fits the area of bone loss 115a, 115b, 115c.

The computer platform may optionally display the 3D computer model 1100. In exemplary embodiments in which the 3D model is displayed, the computer platform may further display the external missing bone surface 117a, 117b, 117c over the area of bone loss 115a, 115b, 115c to allow the viewer to visualize the pre-diseased external missing bone surface 117a, 117b, 117c. Referring back to FIG. 5, the surgeon can use this data to set the posterior pads 693a, 693b of alignment guide 600 to reflect the articular surface of the pre-diseased posterior condyles 103a, 107a.

Figure 16:
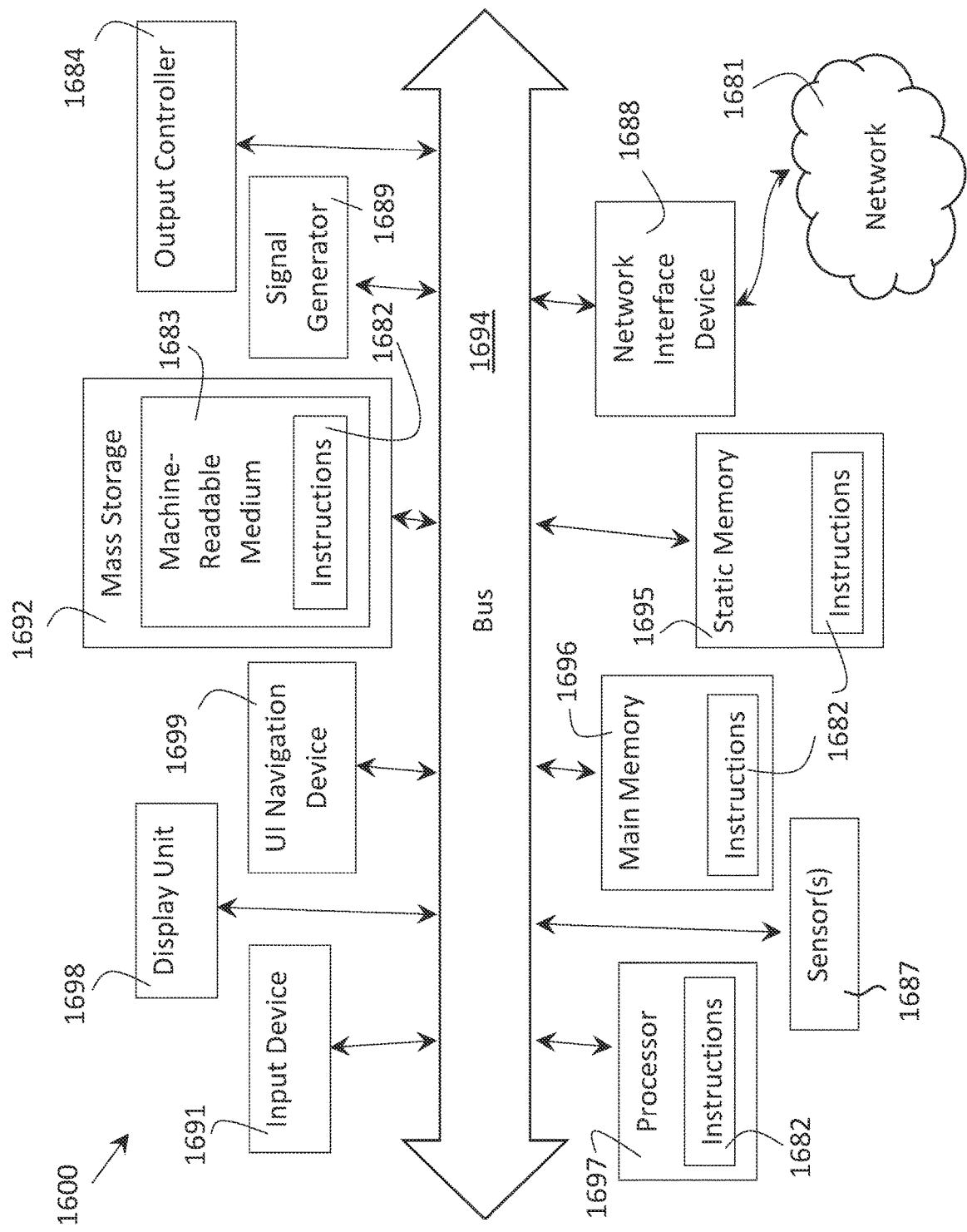
FIG. 16 is a schematic representation of a system configured to generate a physical model of the bone aberration, wherein the physical model is derived from using two or more tissue penetrating, flattened, input images taken of the same subject orthopedic element from calibrated detectors at an offset angle.

FIG. 16 generally depicts a block diagram of an exemplary computational machine 1600 upon which one or more of the methods discussed herein may be performed in accordance with some exemplary embodiments. In certain exemplary embodiments, the computational machine 1600 can operate on a single machine. In other exemplary embodiments, the computational machine 1600 can comprise connected (e.g., networked) machines. Examples of networked machines that can comprise the exemplary computational machine 1600 include by way of example, cloud computing configurations, distributed hosting configurations, and other computer cluster configurations. In a networked configuration, one or more machines of the computational machine 1600 can operate in the capacity of a client machine, a server machine, or both a server-client machine. In exemplary embodiments, the computational machine 1600 can reside on a personal computer ("PC"), a mobile telephone, a tablet PC, a web appliance, a personal digital assistant ("PDA"), a network router, a bridge, a switch, or any machine capable of executing instructions that specify actions to be undertaken by said machine or a second machine controlled by said machine.

Example machines that can comprise the exemplary computational machines 1600 can include by way of example, components, modules, or like mechanisms capable of executing logic functions. Such machines may be tangible entities (e.g., hardware) that is capable of carrying out specified operations while operating. As an example, the hardware may be hardwired (e.g., specifically configured) to execute a specific operation. By way of example, such hardware may comprise configurable execution media (e.g., circuits, transistors, logic gates, etc.) and a computer-readable medium having instructions, wherein the instructions configure the execution media to carry out a specific operation when operating. The configuring can occur via a loading mechanism or under the direction of the execution media. The execution media selectively communicate to the computer-readable medium when the machine is operating. By way of example, when the machine is in operation, the execution media may be configured by a first set of instructions to execute a first action or set of actions at a first point in time and then reconfigured at a second point in time by a second set of instructions to execute a second action or set of actions.

The exemplary computational machine 1600 may include a hardware processor 1697 (e.g., a CPU, a graphics processing unit ("GPU"), a hardware processor core, or any combination thereof, a main memory 1696 and a static memory 1695, some or all of which may communicate with each other via an interlink (e.g., a bus) 1694. The computational machine 1600 may further include a display unit 1698, an input device 1691 (preferably an alphanumeric or character-numeric input device such as a keyboard), and a user interface ("UI") navigation device 1699 (e.g., a mouse or stylus). In an exemplary embodiment, the input device 1691, display unit 1698, and UI navigation device 1699 may be a touch screen display. In exemplary embodiments, the display unit 1698 may include holographic lenses, glasses, goggles, other eyewear, or other AR or VR display components. For example, the display unit 1698 may be worn on a head of a user and may provide a heads-up-display to the user. The input device 1691 may include a virtual keyboard (e.g., a keyboard displayed virtually in a virtual reality ("VR") or an augmented reality ("AR") setting) or other virtual input interface.

The computational machine 1600 may further include a storage device (e.g., a drive unit) 1692, a signal generator 1689 (e.g., a speaker) a network interface device 1688, and one or more sensors 1687, such as a global positioning system ("GPS") sensor, accelerometer, compass, or other sensor. The computational machine 1600 may include an output controller 1684, such as a serial (e.g., universal serial bus ("USB"), parallel, or other wired or wireless (e.g., infrared ("IR") near field communication ("NFC"), radio, etc.) connection to communicate or control one or more ancillary devices.

The storage device 1692 may include a machine-readable medium 1683 that is non-transitory, on which is stored one or more sets of data structures or instructions 1682 (e.g., software) embodying or utilized by any one or more of the functions or methods described herein. The instructions 1682 may reside completely or at least partially, within the main memory 1696, within static memory 1695, or within the hardware processor 1697 during execution thereof by the computational machine 1600. By way of example, one or any combination of the hardware processor 1697, the main memory 1696, the static memory 1695, or the storage device 1692, may constitute machine-readable media.

While the machine-readable medium 1683 is illustrated as a single medium, the term, "machine readable medium" may include a single medium or multiple media (e.g., a distributed or centralized database, or associated caches and servers) configured to store the one or more instructions 1682.

The term "machine-readable medium" may include any medium that is capable of storing, encoding, or carrying instructions for execution by the computational machine 1600 and that cause the computational machine 1600 to perform any one or more of the methods of the present disclosure, or that is capable of storing, encoding, or carrying data structures used by or associated with such instructions. A non-limited example list of machine-readable media may include magnetic media, optical media, solid state memories, non-volatile memory, such as semiconductor memory devices (e.g., electronically erasable programmable read-only memory ("EEPROM"), electronically programmable read-only memory ("EPROM"), and magnetic discs, such as internal hard discs and removable discs, flash storage devices, magneto-optical discs, and CD-ROM and DVD-ROM discs.

The instructions 1682 may further be transmitted or received over a communications network 1681 using a transmission medium via the network interface device 1688 utilizing any one of a number of transfer protocols (e.g., internet protocol ("IP"), user datagram protocol ("UDP"), frame relay, transmission control protocol ("TCP"), hypertext transfer protocol ("HTTP"), etc.) Example communication networks may include a wide area network ("WAN"), a plain old telephone ("POTS") network, a local area network ("LAN"), a packet data network, a mobile telephone network, a wireless data network, and a peer-to-peer ("P2P") network. By way of example, the network interface device 1688 may include one or more physical jacks (e.g., Ethernet, coaxial, or phone jacks) or one or more antennas to connect to the communications network 1681.

By way of example, the network interface device 1688 may include a plurality of antennas to communicate wirelessly using at least one of a single-input multiple-output ("MIMO"), or a multiple-input single output ("M ISO") methods. The phrase, "transmission medium" includes any intangible medium that is capable of storing, encoding, or carrying instructions for execution by the computational machine 1600, and includes analog or digital communications signals or other intangible medium to facilitate communication of such software.

Exemplary methods in accordance with this disclosure may be machine or computer-implemented at least in part. Some examples may include a computer-readable medium or machine-readable medium encoded with instructions operable to configure an electronic device to perform the exemplary methods described herein. An example implementation of such an exemplary method may include code, such as assembly language code, microcode, a higher-level language code, or other code. Such code may include computer readable instructions for performing various methods. The code may form portions of computer program products. Further, in an example, the code may be tangibly stored on or in a volatile, non-transitory, or non-volatile tangible computer-readable media, such as during execution or other times. Examples of these tangible computer-readable media may include, but are not limited to, removable optical discs (e.g., compact discs and digital video discs), hard drives, removable magnetic discs, memory cards or sticks, include removable flash storage drives, magnetic cassettes, random access memories (RAMs), read only memories (ROMS), and other media.

In certain exemplary embodiments, the surface adjustment algorithm can be a curve fitting algorithm. An exemplary curve fitting algorithm may involve interpolation or smoothing. In other exemplary embodiments, the curve fitting algorithm may be used to extrapolate the position of the pre-diseased articular surface of the bone. In other exemplary embodiments, the surface adjustment algorithm can identify the dimensions of a non-worn contralateral orthopedic element 100, such as a non-worn contralateral condyle. The surface adjustment algorithm can add the surface of the non-worn orthopedic element to the corresponding area of bone loss on the worn orthopedic element 100 to calculate the external missing bone surface 117a, 117b. In related exemplary embodiments, an initial missing bone surface calculation based on the measurements of the non-worn orthopedic element 100 can be increased or reduced to fit the curve of the non-worn portions of the worn orthopedic element 100.

In other exemplary embodiments, the surface adjustment algorithm can calculate a maximum depth of bone loss. In a such an embodiment, this maximum depth may be added to the depth of articular cartilage loss to calculate the position of the pre-diseased articular surface for each condyle. In still other embodiments, a volume 61 of the area of bone loss 115a, 115b may be calculated. It will be appreciated that any disclosed calculations or the results of any such calculations may optionally be displayed on a display 19. In other exemplary embodiments, the method may further comprise ascertaining a depth of missing articular cartilage that would have overlaid the external missing bone surface and adding the depth of the missing articular cartilage to the external missing bone surface to define a pre-diseased articular condylar surface.

Figure 13:
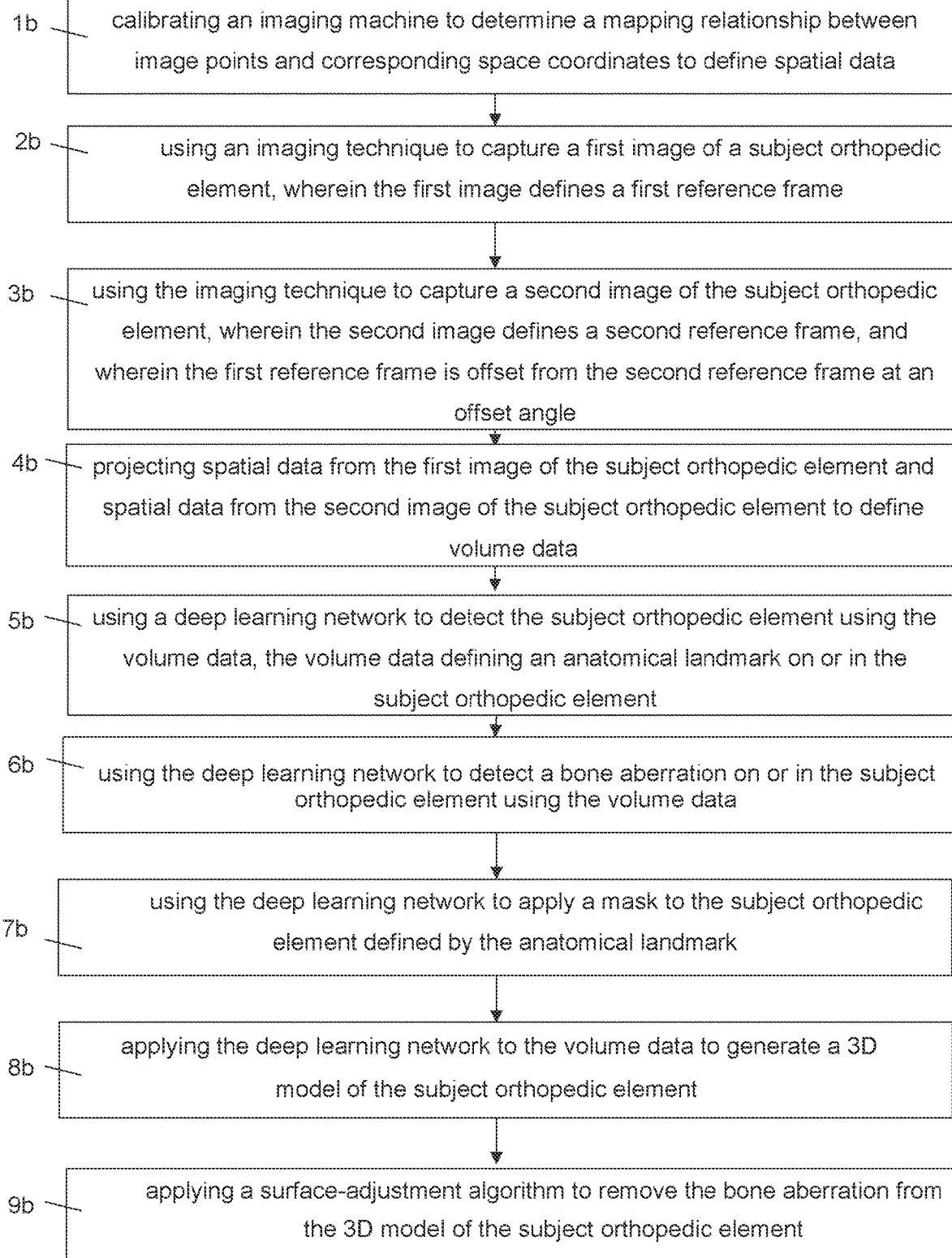
FIG. 13 is a flow chart depicting the steps of another exemplary method.

FIG. 13 is a flow chart that outlines the steps of an exemplary method that uses a deep learning network to identify an area of bone aberration 115 on or in an imaged orthopedic element 100 using two flattened input images taken from an offset angle θ. The exemplary method comprises: Step 1b calibrating an imaging machine to determine a mapping relationship between image points and corresponding space coordinates to define spatial data 43. Step 2b comprises using an imaging technique to capture a first image 30 of a subject orthopedic element 100, wherein the first image 30 defines a first reference frame 30a. Step 3b comprises using the imaging technique to capture a second image 50 of the subject orthopedic element 100, wherein the second image 50 defines a second reference frame 50a, and wherein the first reference frame 30a is offset from the second reference frame 50a at an offset angle θ.

Step 4b comprises projecting spatial data 43 from the first image 30 of the subject orthopedic element 100 and spatial data 43 from the second image 50 of the subject orthopedic element 100 to define volume data 75. Step 5b comprises using a deep learning network to detect the subject orthopedic element 100 using the volume data 75, the volume data 75 defining an anatomical landmark on or in the subject orthopedic element 100.

Step 6b comprises using a deep learning network to detect a bone aberration 115 on or in the subject orthopedic element 100 using the volume data 75. Step 7b comprises using the deep learning network to apply a mask to the subject orthopedic element 100 defined by the anatomical landmark. Step 8b comprises applying the deep learning network to the volume data 75 to generate a 3D model of the subject orthopedic element 100. Step 9b comprises applying a surface adjustment algorithm to remove the bone aberration 115 from the 3D model of the subject orthopedic element 1100.

It will be appreciated in the methods and systems considered to be within the scope of this disclosure, the deep learning network that detects the subject orthopedic element 100, the deep learning network that detects the bone aberration 115, the deep learning network that applies a mask, or generates a 3D model of the bone aberration 115m, or of the orthopedic element 1100, or that applies a surface adjustment algorithm may be the same deep learning network, or may be different deep learning networks. In embodiments in which the deep learning networks are different deep learning networks, these deep learning networks may be referred to as a "first deep learning network," a "second deep learning network," a "third deep learning network," etc.

Figure 14:
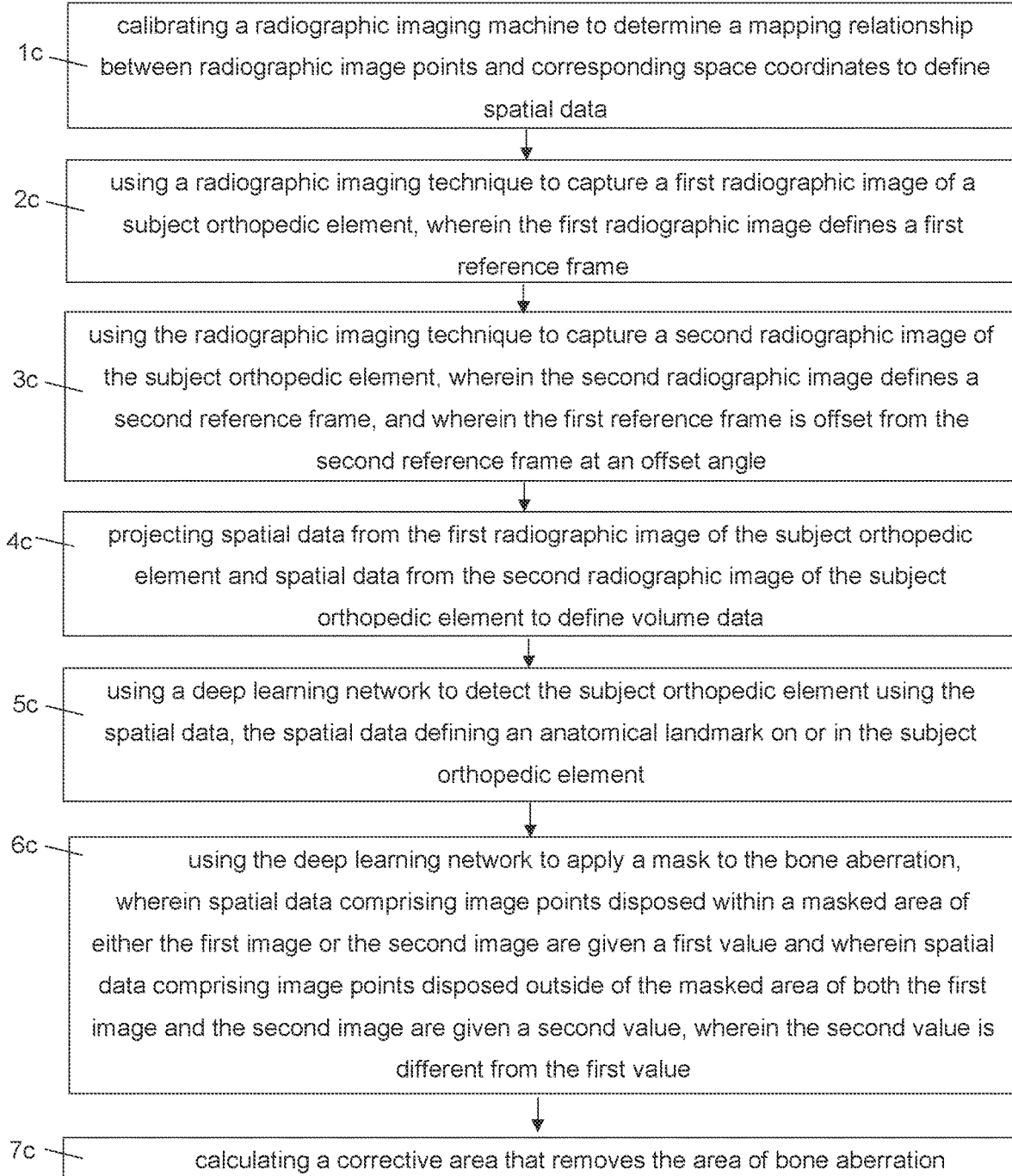
FIG. 14 is a flow chart depicting the steps of yet another exemplary method.

FIG. 14 is a flow chart that outlines the steps of an exemplary method that uses a deep learning network to identify an area of bone aberration 115 on or in an imaged orthopedic element 100 using two flattened input images taken from an offset angle θ. The exemplary method comprises: step 1c calibrating a radiographic imaging machine to determine a mapping relationship between radiographic image points and corresponding space coordinates to define spatial data 43. Step 2c comprises using a radiographic imaging technique to capture a first radiographic image 30 of a subject orthopedic element 100, wherein the first radiographic image 30 defines a first reference frame 30a.

Step 3c comprises using the radiographic imaging technique to capture a second radiographic image 50 of the subject orthopedic element 100, wherein the second radiographic image 50 defines a second reference frame 50a, and wherein the first reference frame 30a is offset from the second reference frame 50a at an offset angle θ. Step 4c comprises projecting spatial data 43 from the first radiographic image 30 of the subject orthopedic element 100 and spatial data 43 from the second radiographic image 50 of the subject orthopedic element 100 to define volume data 75. Step 5c comprises using a deep learning network to detect the subject orthopedic element 100 using the spatial data 43, the spatial data 43 defining an anatomical landmark on or in the subject orthopedic element 100.

Step 6c comprises using the deep learning network to apply a mask to the bone aberration 155, wherein the spatial data 43 comprising image points disposed within a masked area of either the first image or the second image have a first value (e.g., a positive value, or a "1") and wherein the spatial data 43 comprising image points disposed outside of a masked area of either the first image 30 or the second image 50 have a second value (e.g., a negative value, or a "0"), wherein the first value is different from the second value. Step 7c comprises calculating a corrective area that removes the area of bone aberration 115.

Figure 15:
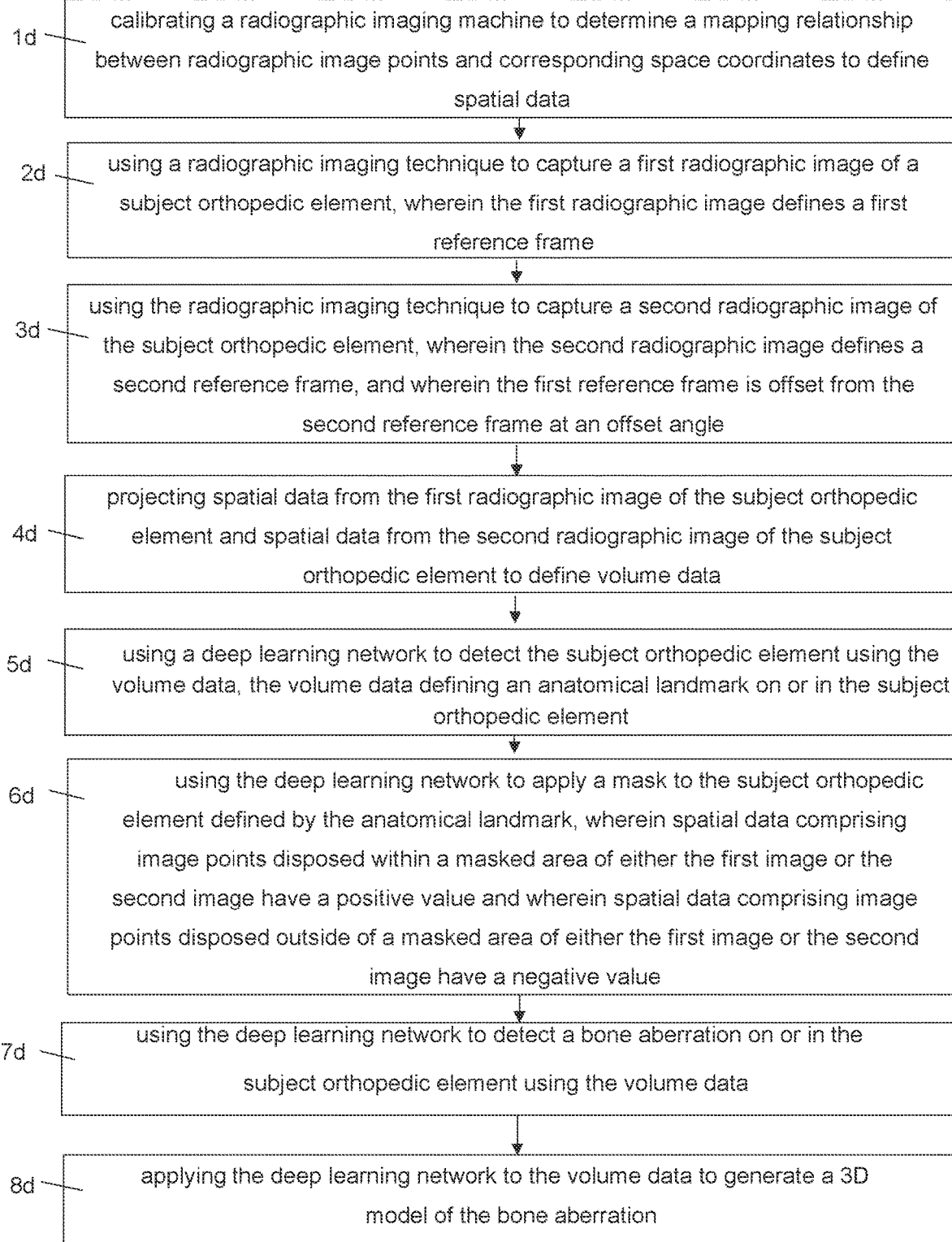
FIG. 15 is a flow chart depicting the steps of still yet another an exemplary method.

FIG. 15 is a flow chart that outlines the steps of an exemplary method that uses a deep learning network to identify an area of bone aberration 115 on or in an imaged orthopedic element 100 using two flattened input images taken from an offset angle θ. The exemplary method comprises: step 1d calibrating a radiographic imaging machine to determine a mapping relationship between radiographic image points and corresponding space coordinates to define spatial data 43.

Step 2d comprises using a radiographic imaging technique to capture a first radiographic image 30 of a subject orthopedic element 100, wherein the first radiographic image 30 defines a first reference frame 30a.

Step 3d comprises using the radiographic imaging technique to capture a second radiographic image 50 of the subject orthopedic element 100, wherein the second radiographic image 50 defines a second reference frame 50a, and wherein the first reference frame 30a is offset from the second reference frame 50a at an offset angle θ. Step 4d comprises projecting spatial data 43 from the first radiographic image 30 of the subject orthopedic element 100 and spatial data 43 from the second radiographic image 50 of the subject orthopedic element 100 to define volume data 75.

Step 5d comprises using a deep learning network to detect the subject orthopedic element 100 using the volume data 75, the volume data 75 defining an anatomical landmark on or in the orthopedic element 100. Step 6d comprises using the deep learning network to apply a mask to the subject orthopedic element 100 defined by the anatomical landmark, wherein spatial data 43 comprising image points disposed within a masked area of either the first image or the second image have a positive value and wherein spatial data 43 comprising image points disposed outside of a masked area of either the first image or the second image have a negative value. Step 7d comprises using a deep learning network to detect a bone aberration 115 on or in the subject orthopedic element 100 using the volume data 75. Step 8d comprises applying the deep learning network to the volume data 75 to generate a 3D model of the bone aberration.

It is further contemplated that the exemplary systems and methods disclosed herein may be used for pre-operative planning, intraoperative planning or execution, or post-operative evaluation of the implant placement and function.

FIG. 18 is a schematic representation of an exemplary system comprising a radiographic imaging machine 1800 comprising an X-ray source 21, such as an X-ray tube, a filter 26, a collimator 27, and a detector 33. In FIG. 18, the radiographic imaging machine 1800 is shown from the top down. A patient 1 is disposed between the X-ray source 21 and the detector 33. The radiographic imaging machine 1800 may be mounted on a rotatable gantry 28. The radiographic imaging machine 1800 may take a radiographic image of the patient 1 from a first reference frame 30a. The gantry 28 may then rotate the radiographic imaging machine 1800 by an offset angle (preferably 90°). The radiographic imaging machine 1800 may then take the second radiographic image 50 from the second reference frame 50a. It will be appreciated that other exemplary embodiments can comprise using multiple input images taken at multiple offset angles θ. In such embodiments, the offset angle may be less than or greater than 90° between adjacent input images.

A transmitter 29 then transmits the first image 30 and the second image 50 to a computational machine 1600. The computational machine 1600 can apply a deep learning network to identify areas of bone aberration 115 on or in an orthopedic element 100 in any manner that is consistent with this disclosure. FIG. 18 further depicts the output of the computational machine 1600 being transmitted to a manufacturing machine 18. The manufacturing machine 18 can be an additive manufacturing machine, such as a 3D printer, or the manufacturing machine can be a subtractive manufacturing machine, such as a CNC machine. In yet other exemplary embodiments, the manufacturing machine 18 can be a casting mold. The manufacturing machine 18 can use the output data from the computational machine 1600 to produce a physical model of one or more 3d models of the subject orthopedic elements 1100. In embodiments, the manufacturing machine can be used to produce a physical 3D model of the bone aberration 115m.

FIG. 18 also depicts another embodiment in which the output data from the computational machine 1600 is transmitted to a display 19. A first display 19a depicts a virtual 3D model of the bone aberration 115m. The second display 19b depicts a virtual 3D model of the identified subject orthopedic element 1100.

In other exemplary embodiments, the 3D model may be displayed on a display 19. This display 19 may take the form of a screen. In other exemplary embodiments, the display 19 may comprise a glass or plastic surface that is worn or held by the surgeon or other people in the operation theater. Such a display 19 may comprise part of an augmented reality device, such that the display shows the 3D model in addition to the bearer's visual field. In certain embodiments, such a 3D model can be superimposed on the actual operative joint. In yet other exemplary embodiments, the 3D model can be "locked" to one or more features of the operative orthopedic element 100, thereby maintaining a virtual position of the 3D model relative to the one or more features of the operative orthopedic element 100 independent of movement of the display 19.

It is still further contemplated that the display 19 may comprise part of a virtual reality system in which the entirety of the visual field is simulated.

An exemplary method for calculating external bone loss for alignment of pre-diseased joints comprises: generating a 3D model of an operative area from at least two 2D radiographic images. At least a first radiographic image is captured at a first transverse position. At least a second radiographic image is captured at a second transverse position. The first transverse position is different than the second transverse position. The first transverse position is desirably orthogonally disposed from the second transverse position. The method further comprises identifying an area of bone loss on the 3D computer model; and applying a surface adjustment algorithm to calculate an external missing bone surface fitting the area of bone loss.

A method for calculating the extent of exterior bone loss comprises: using a radiographic imaging technique to capture a first image of a desired orthopedic element, wherein the first image defines a first reference frame, using the radiographic imaging technique to capture a second image of the desired orthopedic element, wherein the second image defines a second reference frame, and wherein the first frame of reference is offset from the second frame of reference at an offset angle, applying a 3D reconstruction technique to produce a 3D model of the desired orthopedic element, identifying an area of bone loss in the 3D model of the desired orthopedic element, identifying intact areas of bone adjacent to the area of bone loss, applying an adjustment algorithm to display a filled-in area of bone loss.

An exemplary method for calculating external bone loss for alignment of a pre-diseased joint comprises: generating a 3D model of an operative area from at least two 2D radiographic images, wherein at least a first radiographic image is captured at a first position, and wherein at least a second radiographic image is captured at a second position, and wherein the first transverse position is different than the second transverse position; identifying an area of bone aberration on the 3D model; and applying a surface adjustment algorithm to calculate an external missing bone surface configured to replace the area of bone aberration.

In exemplary embodiments, the surface adjustment algorithm is a curve-fitting algorithm. In exemplary embodiments, the method further comprises calculating a maximum depth of the area of bone aberration. In exemplary embodiments, the method further comprises adding the maximum depth of the area of bone aberration to a depth of cartilage wear to define a pre-diseased articular surface. In exemplary embodiments, the 3D model is displayed on an augmented reality device over the real orthopedic element intraoperatively. In exemplary embodiments, the area of bone aberration is an area of bone loss.

In exemplary embodiments, the method further comprises identifying intact areas of a contralateral orthopedic element, wherein the intact areas of the contralateral orthopedic element correspond to the deteriorated area of the operative orthopedic element.

An exemplary method for calculating external bone loss for the purposes of kinematically aligning a pre-diseased knee joint comprises: generating a 3D model of a knee joint operative area from at least two 2D radiographic images, wherein at least a first radiographic image is captured at a first position, and wherein at least a second radiographic image is captured at a second position, and wherein the first position is different than the second position; identifying an area of bone loss on the 3D model, applying a surface adjustment algorithm to calculate an external missing bone surface fitting the area of bone loss; ascertaining a depth of missing articular cartilage that would have overlaid the external missing bone surface; and adding the depth of the missing articular cartilage to the external missing bone surface to define a pre-diseased condylar surface.

In exemplary embodiments, the method further comprises adjusting an adjustable pad of a resection guide locator to touch a remaining external bone surface, such that a guide surface of the resection guide locator is placed at the pre-diseased condylar surface.

An exemplary method for calculating the extent of orthopedic deterioration in vivo comprises: using a non-invasive imaging technique to capture a first image of a desired orthopedic element, wherein the first image defines a first reference frame; using the non-invasive imaging technique to capture a second image of the desired orthopedic element, wherein the second image defines a second reference frame, and wherein the first reference frame is offset from the second reference frame at an offset angle; applying a 3D reconstruction technique to produce a 3D model of the desired orthopedic element; identifying an area of bone loss in the 3D model of the desired orthopedic element; and applying a surface adjustment algorithm to calculate a surface of the deteriorated area.

In exemplary embodiments, the method further comprises projecting the 3D reconstruction model on a display. In exemplary embodiments, the non-invasive imaging technique is a radiographic imaging technique.

An exemplary method for calculating cartilage wear and bone loss for kinematic alignment procedures comprises: calibrating a radiographic imaging machine to determine a mapping relationship between image points and corresponding space coordinates to define spatial data; using a radiographic imaging technique to capture a first image of a desired orthopedic element, wherein the first image defines a first reference frame; using the radiographic imaging technique to capture a second image of the desired orthopedic element, wherein the second image defines a second reference frame, and wherein the first reference frame is offset from the second reference frame at an offset angle; identifying the spatial data of the desired orthopedic element in the first image and the spatial data of the orthopedic element in the second image; transforming the spatial data of the desired orthopedic element in the first image and the second image into a single coordinate system to define transformed spatial data; projecting the transformed spatial data of the desired orthopedic element on a display to produce a 3D model of the desired orthopedic element; identifying a deteriorated area in the 3D model of the desired orthopedic element; and applying a surface adjustment algorithm to calculate a surface of the deteriorated area.

In exemplary embodiments, the adjustment algorithm is a curve-fitting algorithm. In exemplary embodiments, method further comprises displaying the volume of the deteriorated area on the 3D model. In exemplary embodiments, method further comprises identifying an intact area adjacent to the deteriorated area.

An exemplary method for calculating articular cartilage wear and external bone loss on the distal femoral condyles for a kinematic alignment total knee arthroplasty comprises: calibrating a radiographic imaging machine to determine a mapping relationship between image points and corresponding space coordinates to define spatial data; using a radiographic imaging technique to capture a first image of a distal femur, wherein the first image defines a first reference frame; using the radiographic imaging technique to capture a second image of the distal femur, wherein the second image defines a second reference frame, and wherein the first reference frame is offset from the second reference frame at an offset angle; identifying the spatial data of the distal femur in the first image and the spatial data of the distal femur in the second image; transforming the spatial data of the distal femur in the first image and the second image into a single coordinate system to define transformed spatial data; projecting the transformed spatial data of the distal femur on a display to produce a 3D model of the distal femur; identifying a deteriorated area in the 3D model of the distal femur; and applying an adjustment algorithm to calculate a volume of the deteriorated area.

In exemplary embodiments, the first frame of reference is anterior-posterior. In exemplary embodiments, the second frame of reference is medial-lateral. In exemplary embodiments, the deteriorated area comprises missing bone on either of the distal femoral condyles. In exemplary embodiments, the deteriorated area comprises missing articular cartilage on the distal femur. In exemplary embodiments, the adjustment algorithm identifies an intact area adjacent to the deteriorated area.

In exemplary embodiments, the method further comprises identifying intact areas of a contralateral orthopedic element, wherein the intact areas of the contralateral orthopedic element correspond to the deteriorated area of the desired orthopedic element. In exemplary embodiments, the adjustment algorithm is a curve-fitting algorithm. In exemplary embodiments, the method further comprises displaying the volume of the deteriorated area on the 3D model of the distal femur.

An exemplary method for calculating an area of bone aberration comprises: generating a 3D model of a joint operative area from at least two 2D images, wherein a first image is captured at a first transverse position, wherein a second image is captured at a second transverse position, and wherein the first transverse position is different than the second transverse position, identifying an area of a bone aberration on the 3D model, and calculating a corrective area, wherein the corrective area removes the area of bone aberration relative to a surrounding bone area.

In exemplary embodiments, the method further comprises generating a 3D model of the corrective area. In exemplary embodiments, the method further comprises producing a physical 3D model of the corrective area. In exemplary embodiments, the method further comprises producing an orthopedic drill guide comprising the physical 3D model of the corrective area configured to be seated in a corresponding area of negative bone aberration.

In exemplary embodiments, the step of producing a physical 3D model of the corrective area is achieved through an additive manufacturing technique. In exemplary embodiments, the physical 3D model of the corrective area is manufactured from a material selected from the group consisting essential of: a polyamide (i.e., nylon), titanium, cobalt chrome, or another clinically proven biocompatible material. In exemplary embodiments, the method further comprises fixedly engaging the physical 3D model of the corrective area to surgical instrumentation. In exemplary embodiments, the surgical instrumentation is an orthopedic drill guide, and wherein the physical 3D model of the corrective area is configured to be seated in a corresponding area of negative bone aberration. In exemplary embodiments, the method further comprises producing a physical 3D model of the joint operative area, wherein the physical 3D model of the joint operative area comprises of one or more bone elements of the joint operative area.

An exemplary method for calculating an area of bone aberration comprises: using a deep learning network generating a 3D model of a joint operative area from at least two 2D images, wherein a first image is captured at a first transverse position, wherein a second image is captured at a second transverse position, and wherein the first transverse position is different than the second transverse position, identifying an area of a bone aberration on the 3D model, and calculating a corrective area, wherein the corrective area removes the area of bone aberration relative to a surrounding bone area.

An exemplary alignment guide comprises: a body; posterior pads extending from an inferior portion of the body; drill bores extending through the body above the posterior pads; and a physical patient-specific 3D model of a bone aberration engaged to a posterior pad of the posterior pads.

In exemplary embodiments, the patient-specific 3D model of a bone aberration is produced by any system or method of this disclosure.

In exemplary embodiments, the patient-specific 3D model of a bone aberration is produced by a process comprising: calibrating a radiographic imaging machine to determine a mapping relationship between radiographic image points and corresponding space coordinates to define spatial data; using a radiographic imaging technique to capture a first radiographic image of a subject orthopedic element, wherein the first radiographic image defines a first reference frame; using the radiographic imaging technique to capture a second radiographic image of the subject orthopedic element, wherein the second radiographic image defines a second reference frame, and wherein the first reference frame is offset from the second reference frame at an offset angle; projecting spatial data from the first radiographic image of the subject orthopedic element and spatial data from the second radiographic image of the subject orthopedic element; using a deep learning network to detect the subject orthopedic element using the spatial data, the spatial data defining an anatomical landmark on or in the subject orthopedic element; using the deep learning network to detect a bone aberration on or in the subject orthopedic element using the spatial data; and applying the deep learning network to the spatial data to generate the 3D model of the bone aberration.

In another exemplary embodiment, the patient-specific 3D model of a bone aberration is produced by a process comprising: calibrating a radiographic imaging machine to determine a mapping relationship between radiographic image points and corresponding space coordinates to define spatial data; using a radiographic imaging technique to capture a first radiographic image of a subject orthopedic element, wherein the first radiographic image defines a first reference frame; using the radiographic imaging technique to capture a second radiographic image of the subject orthopedic element, wherein the second radiographic image defines a second reference frame, and wherein the first reference frame is offset from the second reference frame at an offset angle; projecting spatial data from the first radiographic image of the subject orthopedic element and spatial data from the second radiographic image of the subject orthopedic element to define volume data; using a deep learning network to detect the subject orthopedic element using the volume data, the volume data defining an anatomical landmark on or in the subject orthopedic element; using the deep learning network to detect a bone aberration on or in the subject orthopedic element using the volume data; and applying the deep learning network to the volume data to generate the 3D model of the bone aberration.

In exemplary embodiments, the physical 3D model of a bone aberration comprises a mating surface that mates with the exposed surface of worn bone. In exemplary embodiments, the physical 3D model of a bone aberration comprises a mating surface, and wherein the mating surface further comprises a projection.

An exemplary system comprising: a 3D model of an orthopedic element comprising an operative area generated from at least two 2D radiographic images, wherein at least a first radiographic image is captured at a first position, and wherein at least a second radiographic image is captured at a second position, and wherein the first position is different than the second position; a computational machine configured to identify an area of bone aberration on the 3D model and further configured to apply a surface adjustment algorithm, wherein the surface adjustment algorithm is configured to remove the area of bone aberration from the 3D model and estimate a topography a bone surface to replace the area of bone aberration.

In exemplary embodiments, the surface adjustment algorithm is a curve-fitting algorithm. In exemplary embodiments, the system further comprises further comprises a display, wherein the 3D model is displayed on the display. In an exemplary embodiment, the display is an augmented reality device or virtual reality device. In an exemplary embodiment, the system further comprises an X-ray imaging machine. In certain exemplary embodiments, the system further comprises a manufacturing device, wherein the manufacturing device is configured to produce a physical model of at least a portion of the 3D model.

In an exemplary embodiment, the manufacturing device is configured to produce a physical model of the bone aberration. In exemplary embodiments, the physical model of the bone aberration is an inverse volume of a negative bone aberration. In an exemplary embodiment, the manufacturing device is an additive manufacturing device. In an exemplary embodiment, the physical model of the bone aberration comprises a medical grade polyamide.

It is to be understood that the present invention is by no means limited to the particular constructions and method steps herein disclosed or shown in the drawings, but also comprises any modifications or equivalents within the scope of the claims known in the art. It will be appreciated by those skilled in the art that the devices and methods herein disclosed will find utility.

What is claimed is:

1. A product comprising a physical 3D model of a bone aberration produced by a process comprising:
   calibrating a radiographic imaging machine to determine a mapping relationship between radiographic image points and corresponding space coordinates to define spatial data;
   using a radiographic imaging technique to capture a first radiographic image of a subject orthopedic element, wherein the first radiographic image defines a first reference frame;
   using the radiographic imaging technique to capture a second radiographic image of the subject orthopedic element, wherein the second radiographic image defines a second reference frame, and wherein the first reference frame is offset from the second reference frame at an offset angle;
   projecting spatial data from the first radiographic image of the subject orthopedic element and spatial data from the second radiographic image of the subject orthopedic element to define volume data;
   using a deep learning network to detect the subject orthopedic element using the volume data, the volume data defining an anatomical landmark on or in the subject orthopedic element;
   using the deep learning network to detect a bone aberration on or in the subject orthopedic element using the volume data;
   applying the deep learning network to the volume data to generate the 3D model of the bone aberration; and
   using a manufacturing technique to produce a physical 3D model of the bone aberration.

2. The product of claim 1, wherein the physical 3D model of the bone aberration comprises a mating surface that mates with the exposed surface of worn bone.

3. The product of claim 1, wherein the physical 3D model of the bone aberration comprises a mating surface, and wherein the mating surface further comprises a projection.

4. A product comprising a physical 3D model of a bone aberration produced by a process comprising:
   calibrating a radiographic imaging machine to determine a mapping relationship between radiographic image points and corresponding space coordinates to define spatial data;
   using a radiographic imaging technique to capture a first radiographic image of a subject orthopedic element, wherein the first radiographic image defines a first reference frame;
   using the radiographic imaging technique to capture a second radiographic image of the subject orthopedic element, wherein the second radiographic image defines a second reference frame, and wherein the first reference frame is offset from the second reference frame at an offset angle;
   projecting spatial data from the first radiographic image of the subject orthopedic element and spatial data from the second radiographic image of the subject orthopedic element;
   using a deep learning network to detect the subject orthopedic element using the spatial data, the spatial data defining an anatomical landmark on or in the subject orthopedic element;
   using the deep learning network to detect a bone aberration on or in the subject orthopedic element using the spatial data;
   applying the deep learning network to the spatial data to generate the 3D model of the bone aberration; and
   using a manufacturing technique to produce a physical 3D model of the bone aberration.

5. The product of claim 4, wherein the physical 3D model of the bone aberration comprises a mating surface that mates with the exposed surface of worn bone.

6. The product of claim 4, wherein the physical 3D model of the bone aberration comprises a mating surface, and wherein the mating surface further comprises a projection.

7. The product of claim 1, wherein the manufacturing technique is an additive manufacturing technique and wherein the physical 3D model of the bone aberration is an inverse volume of a negative bone aberration.

8. The product of claim 1, wherein the physical 3D model of the bone aberration comprises a medical grade polyamide.

9. The product of claim 1, wherein the process further comprises applying a surface adjustment algorithm to the 3D model of the bone aberration, wherein the surface adjustment algorithm is configured to estimate a topography of a bone surface to correct the bone aberration.

10. The product of claim 9, wherein the surface adjustment algorithm is a curve-fitting algorithm.

11. The product of claim 1, wherein the process further comprises displaying a virtual 3D model of the bone on a display.

12. The product of claim 11, wherein the display is an augmented reality device or a virtual reality device.

13. The product of claim 4, wherein the manufacturing technique is an additive manufacturing technique and wherein the physical 3D model of the bone aberration is an inverse volume of a negative bone aberration.

14. The product of claim 4, wherein the physical 3D model of the bone aberration comprises a medical grade polyamide.

15. The product of claim 4, wherein the process further comprises applying a surface adjustment algorithm to the 3D model of the bone aberration, wherein the surface adjustment algorithm is configured to estimate a topography of a bone surface to correct the bone aberration.

16. The product of claim 15, wherein the surface adjustment algorithm is a curve-fitting algorithm.

17. The product of claim 4, wherein the process further comprises displaying a virtual 3D model of the bone on a display.

18. The product of claim 17, wherein the display is an augmented reality device or a virtual reality device.

* * * * *